US012691091B2

(12) United States Patent
Lacorte et al.

(10) Patent No.: US 12,691,091 B2
(45) Date of Patent: *Jul. 28, 2026

(54) COMPOSITIONS COMPRISING CETYLATED FATTY ACIDS FOR USE IN THE TREATMENT OF GASTRIC MUCOSA, DIABETES AND HIGH BLOOD GLUCOSE LEVELS

(71) Applicant: PHARMANUTRA S.P.A., Pisa (IT)

(72) Inventors: Andrea Lacorte, Pisa (IT); Germano Tarantino, Pisa (IT); Elisa Brilli, Pisa (IT)

(73) Assignee: PHARMANUTRA S.P.A., Pisa (IT)

( * ) Notice: Subject to any disclaimer, the term of this patent is extended or adjusted under 35 U.S.C. 154(b) by 843 days.

This patent is subject to a terminal disclaimer.

(21) Appl. No.: 17/613,719

(22) PCT Filed: May 27, 2020

(86) PCT No.: PCT/IB2020/055031

§ 371 (c)(1),
(2) Date: Nov. 23, 2021

(87) PCT Pub. No.: WO2020/240441

PCT Pub. Date: Dec. 3, 2020

(65) Prior Publication Data

US 2022/0226274 A1     Jul. 21, 2022

(30) Foreign Application Priority Data

May 27, 2019     (IT) ........................ 102019000007329

(51) Int. Cl.
*A61K 31/231* (2006.01)
*A61K 31/05* (2006.01)
*A61K 47/10* (2017.01)
*A61P 1/04* (2006.01)

(52) U.S. Cl.
CPC ............ *A61K 31/231* (2013.01); *A61K 31/05* (2013.01); *A61K 47/10* (2013.01); *A61P 1/04* (2018.01)

(58) Field of Classification Search
CPC .... A61K 2300/00; A61K 31/05; A61K 31/23; A61K 31/231; A61K 45/06; A61K 47/10; A61K 47/44; A61K 9/0053; A61P 1/04; A61P 1/16; A61P 3/04; A61P 3/10
See application file for complete search history.

(56) References Cited

U.S. PATENT DOCUMENTS

| | | |
|---|---|---|
| 4,113,881 A | 9/1978 | Diehl |
| 4,393,133 A | 7/1983 | Knowles et al. |
| 5,888,563 A | 3/1999 | Mehansho et al. |
| 6,039,978 A | 3/2000 | Bangs et al. |
| 6,361,800 B1 | 3/2002 | Cooper et al. |
| 6,417,227 B1 | 7/2002 | Lord et al. |
| 8,404,745 B2 | 3/2013 | Barathur et al. |
| 9,861,670 B2 | 1/2018 | Clements et al. |
| 10,597,608 B2 | 3/2020 | Lacorte et al. |
| 12,246,036 B2 | 3/2025 | Lacorte et al. |
| 12,297,406 B2 | 5/2025 | Lacorte et al. |
| 12,383,525 B2 | 8/2025 | Lacorte et al. |
| 2002/0058705 A1 | 5/2002 | Gonzales Bravo et al. |
| 2003/0181521 A1 | 9/2003 | Leonard et al. |
| 2005/0100636 A1 | 5/2005 | Botteri et al. |
| 2005/0261257 A1 | 11/2005 | Vermeer |
| 2007/0065521 A1 | 3/2007 | Venkataraman et al. |
| 2007/0148258 A1 | 6/2007 | O'Neill et al. |
| 2007/0148259 A1 | 6/2007 | Gupta |
| 2009/0186939 A1 | 7/2009 | Chan et al. |
| 2009/0326060 A1 | 12/2009 | Chan et al. |
| 2010/0021573 A1 | 1/2010 | Gonzalez et al. |
| 2011/0054030 A1 | 3/2011 | Petraglia et al. |
| 2011/0294665 A1 | 12/2011 | Makino |
| 2012/0265119 A1 | 10/2012 | Barathur et al. |
| 2013/0157974 A1 | 6/2013 | Ziegler et al. |
| 2014/0121156 A1 | 5/2014 | Hausman |

(Continued)

FOREIGN PATENT DOCUMENTS

| | | |
|---|---|---|
| CN | 106343566 A | 1/2017 |
| CN | 108137472 A | 6/2018 |

(Continued)

OTHER PUBLICATIONS

European Food Safety Authority, Scientific Opinion on the Safety of 'Cetyl Myristoleate Complex' as a food ingredient, EFSA Journal, 8 (Year: 2010).*
Shimoyama (Challenges to Unravel Mechanisms of GERD, Gastroesophageal Reflux Disease—Theory and Research) (Year: 2018).*
Ulatowski et. al. (Neurobiology of Disease, 84, 78-83) (Year: 2015).*
Machine Translation of WO2010117194A2 (Year: 2010).*
Advisory Action for U.S. Appl. No. 16/631,426, filed Jan. 15, 2020 on behalf of Pharmanutra S.P.A. Mail Date: Dec. 20, 2022. 4 Pages.
Aoun, M. et al. "High Dephosphorylated-Uncarboxylated MGP in Hemodialysis patients: risk factors and response to vitamin K2, a pre-post intervention clinical trial", BMC Nephrology, Jun. 2017, vol. 18, 191. 10 pages.

(Continued)

*Primary Examiner* — Jeffrey H Murray
*Assistant Examiner* — Daniel John Burkett
(74) *Attorney, Agent, or Firm* — Steinfl + Bruno LLP

(57) ABSTRACT

A composition is described comprising a mixture of at least one cetylated fatty acid or a mixture of cetylated fatty acids and an antioxidant in reduced percentages by weight, and related methods for treatment of arthritis and of inflammatory joint and musculoskeletal pain. Furthermore a composition is described comprising a mixture of at least one cetylated fatty acid or a mixture of cetylated fatty acids and, optionally, an antioxidant, and related treatment methods for protecting the gastric mucosa and for regulating the blood glucose levels. Additionally, a method is described for preparing the at least one cetylated fatty acid or mixture of cetylated fatty acids and for preparing compositions comprising the cetylated fatty acids and the antioxidant.

18 Claims, 8 Drawing Sheets

(56) References Cited

U.S. PATENT DOCUMENTS

| | | | |
|---|---|---|---|
| 2014/0322314 A1* | 10/2014 | Fawzy | A61K 47/186 |
| | | | 424/456 |
| 2015/0250885 A1 | 9/2015 | Lacorte et al. | |
| 2016/0008415 A1 | 1/2016 | Clements et al. | |
| 2016/0310445 A1 | 10/2016 | Vermeer | |
| 2017/0056465 A1 | 3/2017 | Tobin et al. | |
| 2017/0080023 A1* | 3/2017 | Agam | A61K 9/4875 |
| 2017/0112178 A1 | 4/2017 | Perrin et al. | |
| 2017/0202802 A1 | 7/2017 | Fernandez et al. | |
| 2018/0098962 A1 | 4/2018 | Bromley | |
| 2019/0016991 A1 | 1/2019 | Lacorte et al. | |
| 2020/0085710 A1 | 3/2020 | Denda et al. | |
| 2020/0206157 A1 | 7/2020 | Lacorte et al. | |
| 2020/0246377 A1 | 8/2020 | Lacorte et al. | |
| 2022/0211655 A1* | 7/2022 | Lacorte | A61K 31/122 |
| 2022/0220414 A1 | 7/2022 | Lacorte et al. | |
| 2025/0270472 A1 | 8/2025 | Lacorte et al. | |

FOREIGN PATENT DOCUMENTS

| | | | | | |
|---|---|---|---|---|---|
| EP | 0679394 A2 | 11/1995 | | | |
| EP | 2380578 A1 | 10/2011 | | | |
| EP | 2886129 A1 | 6/2015 | | | |
| GB | 2552952 A | 2/2018 | | | |
| JP | S5841813 A | 3/1983 | | | |
| JP | S6351312 A | 3/1988 | | | |
| JP | H04154724 A | 5/1992 | | | |
| JP | H08253415 A | 10/1996 | | | |
| JP | 2002515866 A | 5/2002 | | | |
| JP | 2003342159 A | 12/2003 | | | |
| JP | 2007523056 A | 8/2007 | | | |
| JP | 2009525277 A | 7/2009 | | | |
| JP | 2015523409 A | 8/2015 | | | |
| NZ | 332959 A | 9/2001 | | | |
| WO | 1997/031620 A2 | 9/1997 | | | |
| WO | 00/64436 A1 | 11/2000 | | | |
| WO | 03/018731 A1 | 3/2003 | | | |
| WO | 2004/019923 A1 | 3/2004 | | | |
| WO | 2004/084829 A2 | 10/2004 | | | |
| WO | 2004/084829 A3 | 1/2005 | | | |
| WO | 2005/044189 A2 | 5/2005 | | | |
| WO | 2007/089577 A2 | 8/2007 | | | |
| WO | 2010/079514 A1 | 7/2010 | | | |
| WO | WO-2010117194 A2 * | 10/2010 | | | A61K 31/20 |
| WO | 2012/161572 A1 | 11/2012 | | | |
| WO | 2014/009806 A1 | 1/2014 | | | |
| WO | 2014/160279 A1 | 10/2014 | | | |
| WO | 2016/131993 A2 | 8/2016 | | | |
| WO | 2017/029580 A1 | 2/2017 | | | |
| WO | 2018/034797 A1 | 2/2018 | | | |
| WO | 2018/221534 A1 | 12/2018 | | | |
| WO | 2019/021232 A1 | 1/2019 | | | |
| WO | 2019/025922 A1 | 2/2019 | | | |
| WO | 2020/240438 A1 | 12/2020 | | | |
| WO | 2020/240441 A1 | 12/2020 | | | |
| WO | 2020/240443 A1 | 12/2020 | | | |
| WO | 2024/184848 A1 | 9/2024 | | | |

OTHER PUBLICATIONS

Barisani et al. "Iron overload and gene expression in HepG2 cells: analysis by differential display" *FEBS Letters* 2000, 469, 208-212.

Barpanda P et al. "Sodium iron pyrophosphate: a novel 3.0V iron-based cathode for sodium-ion batteries", Electrochemistry Communications, vol. 24, Oct. 2012, pp. 116-119.

Breymann, Prof. Dr. Christian. Preventing and Treating Iron Deficiency Anaemia in Pregnant Women. Are we doing our best? Presentation in Zurich, Switzerland, May 15, 2017. 27 pages.

Commission Directive 96/77/EC of Dec. 2, 1996; last amendment M7 Commission Directive 2006/129/EC of Dec. 8, 2006. 165 pages.

Commission Regulation (EU) No. 231/2012 of Mar. 9, 2012. Specifications for food additives listed on Annexes II and III to Regulation (EC) No. 1333/2008 of the European Parliament and of the Council. Official Journal of the European Union. 295 pages.

"Coordination Complex" from Wikipedia, through the Wayback Machine dated Nov. 18, 2016. 10 pages.

The Regulation (EC) No. 1333/2008 of the European Parliament and of the Council of Dec. 16, 2008 on food additives. Dated: Mar. 22, 2023. pp. 346.

Cutcliffe T et al., "Vitamin K2 may reverse calcification of blood vessels in people with kidney disease" *NUTRA Ingredients*, Jun. 2017, 3 pages.

Decision of Rejection for Japanese Application No. 2020-502672 filed on Jul. 26, 2018 on behalf of Pharmanutra S.P.A. Dated Jan. 4, 2023. 9 pages.

"E number" from European Food Safety Authority, Downloaded Jul. 21, 2023. 1 page. Website: www.efsa.europa.eu/en/glossary/e-number#:~:text=A%20number%20used%20in%20the,has%20been%20apprvoed%20for%20use.

E322-Lechitins: on the web site of INCHEM (Internationally Peer Reviewed Chemical Safety Information), World Health Organization, the following Summary of Evaluations Performed by the Joint FAO/WHO Expert Committee on Food Additives dated Feb. 6, 2004. 1 page. [website: inchem.org/documents/jecfa/jeceval/jec_1261.htm].

Erni, I. Oswald N. et al. "Chemical characterization of iron (III)-hydroxide-dextrin complexes. A comparative study of commercial preparations with alleged reproductions used in the examination of bioavailability", Arzneimittelforschung, 1984: 34 (11): 1555-9. (Abstract only). 1 page.

EUR-Lex, Access to European Union Law, Document 51977PC0304. Proposal for a Council Directive amending for the first time Directive 74/329/EEC on the approximation of the laws of the Member States relating to emulsifiers, stabilizers, thickeners ang gelling agents for use in foodstuffs (submitted to the Council by the Commission) Dated Jul. 4, 1977. 12 pages. Website: eur-lex.europa. eu/legal-content/EN/TXT/?uri=CELEX%3A51977PC0304&qid=1685448865117.

Final Office Action for U.S. Appl. No. 16/631,426, filed Jan. 15, 2020 on behalf of Pharmanutra S.P.A. Mail Date: Aug. 11, 2022. 18 Pages.

Final Office Action for U.S. Appl. No. 16/635,516, filed Jan. 30, 2020 on behalf of Pharmanutra S.P.A. Mail Date: Dec. 1, 2021 15 pages.

Final Office Action for U.S. Appl. No. 16/635,516, filed Jan. 30, 2020 on behalf of Pharmanutra S.P.A. Mail Date: Feb. 22, 2023. 18 pages.

Firdaus S et al. "Green synthesis of silver nanoparticles using Carica Papaya fruit extract under sunlight irradiation and their colorimetric detection of mercury ions", 2nd International Symposium on Frontier of Applied Physics, IOP Conf Series: Journal of Physics: Conf. Series 817 (2017) 012029. 6 pages. Doi: 10.1088/1742-6596/817/1/012029.

"Food additives" from European Food Safety Authority, Downloaded Jul. 21, 2023. 9 pages. Website: www.efsa.europa.eu/en/topics/topic/food-additives.

"Food additives" from European Food Safety Authority (EFSA), Downloaded though the Wayback Machine for Jul. 17, 2017. 2 pages. Website: www.efsa.europa.eu/en/topics/topic/food-additives.

Garrelds, I. M. et al. "Time dependent production of cytokines and eicosanoids by human monocytic leukaemia U937 cells; effects of glucocorticosteroids" *Mediators Inflamm*, 1999, 8, 229-235.

Geisser, P. et al. Review: The Pharmacokinetics and Pharmacodynamics of Iron Preparations. Pharmaceutics, (Jan. 2011) 3, pp. 12-33. Doi.org/10.3390/pharmaceutics3010012. Website: mdpi.com/journal/pharmaceutics.

Geisser, Peter. Safety and Efficacy of Iron(III)-hydroxide Polymaltose Complex. Arzneimittel-Forschung (Drug Research) 2007: 57 (6a): 439-452.

Gupta A., et al. "Dialysate iron therapy: Infusion of soluble ferric pyrophosphate via the dialysate during hemodialysis" Kidney International (1999); 55(5):1891-1898.

Huang, Z.B. et al. "HMGB1 release by human liver L02 and HepG2 cells induced by lipopolysaccharide" *Molecular Medicine Reports* 8:103-112, 2013.

(56)        References Cited

OTHER PUBLICATIONS

Ilbert, Marianne et al., "Review: Insight into the evolution of the iron oxidation pathways", Biochimica et Biophysica Acta, 1827 (2013), pp. 161-175.
International Preliminary Report on Patentability for International Application No. PCT/IB2018/055586 filed on Jul. 26, 2018 on behalf of Pharmanutra S.P.A. Mail Date: Jan. 28, 2020 7 pages.
International Preliminary Report on Patentability for International Application No. PCT/IB2018/055634 filed on Jul. 27, 2018 on behalf of Pharmanutra S.P.A. Mail Date: Feb. 4, 2020 8 pages.
International Preliminary Report on Patentability for International Application No. PCT/IB2020/055028 filed on May 27, 2020 on behalf of Alesco S.R.L. Mail Date: Nov. 16, 2021 7 pages.
International Preliminary Report on Patentability for International Application No. PCT/IB2020/055031 filed on May 27, 2020 on behalf of Alesco S.R.L. Mail Date: Nov. 16, 2021 9 pages.
International Preliminary Report on Patentability for International Application No. PCT/IB2020/055037 filed on May 27, 2020 on behalf of Alesco S.R.L. Mail Date: Nov. 16, 2021 6 pages.
International Search Report and Written Opinion for International Application No. PCT/IB2018/055586 filed on Jul. 26, 2018 on behalf Pharmanutra S.P.A. Mail Date: Oct. 25, 2018 11 pages.
International Search Report and Written Opinion for International Application No. PCT/IB2018/055634 filed on Jul. 27, 2018 on behalf Pharmanutra S.P.A. Mail Date: Dec. 4, 2018 12 pages.
"Iron Dextran" from DrugBank, DrugBank Accession No. DB00893, dated Nov. 26, 2012, 14 pages.
"Iron polymaltose" from Wikipedia, Downloaded: Jul. 23, 2023. 5 pages. Website: en.wikipedia.org/wiki/Iron_polymaltose.
"Iron Sucrose" from Wikipedia, through the Wayback Machine dated Oct. 22, 2016. 1 page.
Kidney disease—*Wikipedia*, Dated: May 6, 2017, 7 pages.
Liu, H.Z. et al. "The U937 cell line induced to express CD14 protein by 1,25-dihydroxyvitamin D3 and be sensitive to endotoxin stimulation" *Hepatobiliary Pancreat. Dis. Int.* 2005, vol. 4, No. 1, 84-89.
Miki, K. et al. "Extracellular activation of arginase-1 decreases enterocyte inducible nitric oxide synthase activity during systemic inflammation" *Am J Physiol Gastrointest Liver Physiol.* 2009; 297(4): G840-G848.
Muriuki J.M. et al., "Malaria is a cause of iron deficiency in African children" *Nature Medicine*, vol. 27, Apr. 2021, pp. 653-658. 19 pages.
Neven E. et al., "Iron and vascular calcification. Is there a link" *Nephrol Dial Transplant*, Feb. 2011, 26, pp. 1137-1145.
Nicoll, R. et al. "A Review of the Effect of Diet on Cardiovascular Calcification", Int. J. Mol. Sci., (2015), vol. 16, pp. 8861-8883. ISSN 0004771926.
Non-Final Office Action for U.S. Appl. No. 16/631,426, filed Jan. 15, 2020 on behalf of Pharmanutra S.P.A. Mail Date: Feb. 2, 2023. 17 Pages.
Non-Final Office Action for U.S. Appl. No. 16/631,426, filed Jan. 15, 2020 on behalf of Pharmanutra S.P.A. Mail Date: Nov. 10, 2021 17 pages.
Non-Final Office Action for U.S. Appl. No. 16/635,516, filed Jan. 30, 2020 on behalf of Pharmanutra S.P.A. Mail Date: Jul. 26, 2022 18 pages.
Non-Final Office Action for U.S. Appl. No. 16/635,516, filed Jan. 30, 2020 on behalf of Pharmanutra S.P.A. Mail Date: May 12, 2021 30 pages.
Opinion of the Scientific Panel on Food Additives, Flavourings, Processing Aids and Material in Contact with Food on Sucrose esters of fatty acids, e 473 and sucroglycerides, E 474 based on a request from the Commission related to Sucrose Esters of Fatty Acids (E 473). Question No. EFSA-Q-2003-139. Adopted on Oct. 7, 2004; Modified on Jan. 25, 2006. The EFSA Journal (2004) 106, 1-23.
Ozcelik, Berrin. "Fungi/Bactericidal and Static Effect of Ultraviolet Light in 254 and 354 nm wavelengths" *Research Journal of Microbiology* 2007 2 (1): 42-49.

Pepys, M. et al., C-reactive protein: a critical update *J. Clin. Invest.* 2003, 111 (12): 1805-1812.
Restriction Requirement for U.S. Appl. No. 16/631,426, filed Jan. 15, 2020 on behalf of Pharmanutra S.P.A. Mail Date: Aug. 20, 2021 10 pages.
Rincon, M. "Interleukin-6: from an inflammatory marker to a target for inflammatory diseases" Trends in Immunology, Nov. 2012, vol. 33, No. 11, pp. 571-577.
Saliou, C. et al. "Selective inhibition of NF-KB activation by the flavonoid hepatoprotector silymarin in HepG2, Evidence for different activating pathways" *FEBS Letters*, 1998, 440, 8:12.
"Salt (chemistry)" from Wikipedia, through the Wayback Machine dated Feb. 11, 2016. 4 pages.
Search of Search Food Additives Database for "E473" from European Food Safety Authority, Downloaded Jul. 21, 2023. 3 pages. Website: food.ec.europa.eu/safety/food-improvement-agents/additives/database_en.
Shelley, C. S. et al. "During Differentiation of the Monocytic Cell Line U937, PurAlpha Mediates Induction of the CD11c Beta2 Integrin Gene Promoter" *J Immunol*, 2002, 168, 3887-3893.
SiderAL product page on Pharmanutra website. 2 pages. Printed Jul. 21, 2023. Website: www.pharmanutra.it/en/brand/pharmanutra/sideral/.
Sideral.it website. Printed May 19, 2023. 11 pages.
Smith, E. M.; Tangpricha, V. "Vitamin D and Anemia: Insights into an Emerging Association". Curr Opin Endocrinol Diabetes Obes, Dec. 2015, 22(6), 432-438. 14 pages.
Sonou, T. et al., "Magnesium prevents phosphate-induced vascular calcification via TRPM7 and Pit-1 in an aortic tissue culture model". Hypertension Research, (2017), vol. 40, pp. 562-567. ISSN 0004771924.
Spiegel D.M. et al., "Long-term effects of magnesium carbonate on coronary artery calcification and bone mineral density in hemodialysis patients: a pilot study" *Hemodial Int.*, Oct. 2009 (Abstract Only) 13(4): 453-9.
Strober W. "Trypan blue exclusion test of cell viability" *Curr Protoc Immunol.* May 2001; 111: (A3.B1-A3-B3), Appendix 3: Appendix 3B. 3 pages.
Toblli, J.E. et al., Iron(III)-hydroxide Polymaltose Complex in Iron Deficiency Anemia. Review and Meta-analysis. Arzneimittel-Forschung (Drug Research) 2007: 57 (6a): 431-438.
Villarroel P. et al. "Interleukin 6 and lipopolysaccharide modulate hepcidin mRNA expression by HepG2 cells" *Biol Trace Elem Res.* Dec. 2012;150(1-3):496-501.
Wikipedia page for "International Numbering System for Food Additives" dated Dec. 22, 2016 (16 pp).
Wikipedia page for "E number" dated Jul. 17, 2017 (29 pp).
Zughaier, S.M. et al. "The role of vitamin D in regulating the iron-hepcidin-ferroportin axis in monocytes" *J Clin Transl Endocrinol* (2014) e19-e25.
Final Office Action for U.S. Appl. No. 16/631,426, filed Jan. 15, 2020 on behalf of Pharmanutra S.P.A. Mail Date: Nov. 16, 2023. 17 Pages.
Non-Final Office Action for U.S. Appl. No. 16/635,516, filed Jan. 30, 2020 on behalf of Pharmanutra S.P.A. Mail Date: Oct. 4, 2023. 25 pages.
O'Neill, W.C. et al. "Plasma pyrophosphate and vascular calcification in chronic kidney disease", Nephrol Dial Transplant (2010), 25: 187-191. Doi: 10.1093/ndt/gfp362.
O'Neill, W.C. et al. "Treatment with pyrophosphate inhibits uremic vascular calcification", Kidney Int, Mar. 2011, 76(5): 512-517. 15 pages. Doi: 10.1038/ki.2010.461.
Shah, R.B. et al., "Pharmaceutical characterization and thermodynamic stability. Assessment of a colloidal iron drug product: Iron sucrose", International Journal of Pharmaceutics, 464 (Jan. 17, 2014), pp. 46-52.
Fragala M.S. et al: "Influences of a dietary supplement in combination with an exercise and diet regimen on adipocytokines and adiposity in women who are overweight", European Journal of Applied Physiology, vol. 105, No. 5. 2009, pp. 665-672.
International Search Report for International Application No. PCT/IB2020/055028 filed on May 27, 2020 on behalf of Alesco S.R.L. Mail Date: Sep. 9, 2020 4 pages.

(56)          References Cited

OTHER PUBLICATIONS

International Search Report for International Application No. PCT/IB2020/055031 filed on May 27, 2020 on behalf of Alesco S.R.L. Mail Date: Aug. 28, 2020 5 pages.
International Search Report for International Application No. PCT/IB2020/055037 filed on May 27, 2020 on behalf of Alesco S.R.L. Mail Date: Sep. 10, 2020 4 pages.
Written Opinion for International Application No. PCT/IB2020/055028 filed on May 27, 2020 on behalf of Alesco S.R.L. Mail Date: Sep. 9, 2020 6 pages.
Written Opinion for International Application No. PCT/IB2020/055031 filed on May 27, 2020 on behalf of Alesco S.R.L. Mail Date: Aug. 28, 2020 8 pages.
Written Opinion for International Application No. PCT/IB2020/055037 filed on May 27, 2020 on behalf of Alesco S.R.L. Mail Date: Sep. 10, 2020 5 pages.
Bagirova, V.L. et al. (1998) No. 6. C. 34-36. Russian original + English extract. 8 pages. (D6).
Barot, B.S. et al. Physicochemical and structural characterization of iron-sucrose formulations: a comparative study. Pharmaceutical Development and Technology. (Published online May 23, 2013) 19 (5): 513-520. 9 pages.
First Notification of Office Action for Chinese Application No. 202080039453.9 on behalf of Alesco S.R.L Pharmanutra S.P.A. Issued on Feb. 3, 2024. 3 pages. English translation only.
First Notification of Office Action for Chinese Application No. 202080039535.3 on behalf of Alesco S.R.L Pharmanutra S.P.A. Issued on Feb. 2, 2024. 9 pages. Original + English translation.
First Notification of Office Action for Chinese Application No. 202080039600.2 on behalf of Alesco S.R.L Pharmanutra S.P.A. Issued on Feb. 2, 2024. 10 pages. Original and English translation.
Gomez-Ramirez, Susana et al. Sucrosomial® Iron: A New Generation Iron for Improving Oral Supplementation. Pharmaceuticals. (2018). 11, 97. 23 pages. DOI:10.3390/ph11040097. Website: mdpi.com/journal/pharmaceutical.
Search Report from the Intellectual Property Office of Singapore for Application No. 11202112774X filed on May 27, 2020. Mailed on Aug. 17, 2023. 2 pages. Issued in English.
Search Report from the Intellectual Property Office of Singapore for Application No. 11202112779Y filed on May 27, 2020. Mailed on Aug. 17, 2023. 2 pages. Issued in English.
The Eurasian Patent Office Application No. 202193083/28, Conclusion on patentability of the invention. Mailed on Dec. 19, 2022. 11 pages. Russian and partial English translation.
The Eurasian Patent Office Application No. 202193083/28, Conclusion on patentability of the invention. Mailed on Jul. 19, 2023. 18 pages. Russian and partial English translation.
Wikipedia, The Free Encyclopedia, "Pourbaix diagram", (Dec. 11, 2017). Downloaded on Mar. 29, 2024. 8 pages.
Wikipedia, The Free Encyclopedia, "Sucrose", (Dec. 31, 2017). Downloaded on Mar. 29, 2024. 24 pages.
Wikipedia, The Free Encyclopedia, "Sucrose esters", (Nov. 16, 2017). Downloaded on Mar. 29, 2024. 7 pages.
Written Opinion from the Intellectual Property Office of Singapore for Application No. 11202112774X filed on May 27, 2020. Mailed on Aug. 21, 2023. 7 pages. Issued in English.
Written Opinion from the Intellectual Property Office of Singapore for Application No. 11202112779Y filed on May 27, 2020. Issued on Aug. 21, 2023. 7 pages. Issued in English.
Basson, M.D. Hierarchies of Healing in Gut Mucosal Injury.Journal of Physiology and Pharmacology, (2017), 68, 6, 789-795.
Birrell M. A. et al., "Anti-inflammatory effects of PGE2 in the lung: role of the EP4 receptor subtype" Thorax BMJ Journals, May 2015, pp. 740-747.
Buthelezi N. M. D. et al., "Destructive and non-destructive techniques used for quality evaluation of nuts: A review" Scientia Horticulturae 247, (2019), pp. 138-146.
Cho J. et al., "Prostaglandin E2 Induces IL-6 and IL-8 Production by the EP Receptors/Akt/NF-KB Pathways in Nasal Polyp-Derived Fibroblasts" Allergy Asthma Immunol Res., Sep. 2014, pp. 449-457.

Chung, B. et al. "Oncostatin M is a potent inducer of hepcidin, the iron regulatory hormone", The FASEB Journal, Jun. 2010, vol. 24, 2093-2103.
Clamp, J.R, et al. The Gastric Mucosal Barrier, Methods Find Exp Clin Pharmacol., (1989), 11 Suppl 1:19-25. Abstract Only.
"Converting Units of Measure for Folate, Niacin, and Vitamins A, D, and E on the Nutrition and Supplement Facts Labels: Guidance for Industry", U.S. Dept of Health and Human Services, Food and Drug Administration, Center for Food Safety and Applied Nutrition, Aug. 2019. 31 pages. Website: www.fda.gov/FoodGuidances.
Hinson R. G. et al., "Elevated interleukin 6 is induced by prostaglandin E2 in a murine model of inflammation: Possible role of cyclooxygenase-2" Proc. Natl. Acad. Sci. USA, vol. 93, May 1996, pp. 4885-4890.
Liu X.-H. et al., "Cross-Talk between the Interleukin-6 and Prostaglandin E2 Signaling systems Results in Enhancement of Osteoclastogenesis through Effects on the Osteoprotegerin/Receptor Activator of Nuclear Factor-KB (RANK) Ligand/RANK System" Endocrinology 146(4), Dec. 23, 2004, 8 pages.
McCarty, M.F. et al. "Bioavailable dietary phosphate, a mediator of cardiovascular disease, may be decreased with plant-based diets, phosphate binder, niacin, and avoidance of phosphate additives", Nutrition, (Jul.-Aug. 2014), vol. 30, Issues 7-8, pp. 739-747. ISSN 0004771923.
Non-Final Office Action for U.S. Appl. No. 17/614,294, filed Nov. 24, 2021 on behalf of Alesco S.R.L et al. Mailed on Aug. 28, 2024. 23 pages.
Non-Final Office Action issued for U.S. Appl. No. 17/613,886, filed Nov. 23, 2021 on behalf of Alesco S.R.L. and Pharmanutra S.P.A. Mailed on Aug. 1, 2024. 25 pages.
Notice of Allowance for U.S. Appl. No. 16/635,516, filed Jan. 30, 2020 on behalf of Pharmanutra S.P.A. Mail Date: Jul. 31, 2024. 15 pages.
Notice of Allowance for U.S. Appl. No. 16/635,516, filed Jan. 30, 2020 on behalf of Pharmanutra S.P.A. Mail Date: Nov. 20, 2024. 10 pages.
Notice of Allowance issued for U.S. Appl. No. 17/613,886, filed Nov. 23, 2021 on behalf of Alesco S.R.L. and Pharmanutra S.P.A. Mailed on Jan. 8, 2025. 10 pages.
Notice of Reasons for Refusal for Japanese Application No. 2021-570463 filed May 27, 2020. Mailed on May 7, 2024. Original and Machine translation. 13 pages.
Office Action Summary (Examination Result) for United Arab Emirates Application No. P6002147/2021 filed on Nov. 24, 2021. 5 pages.
"Peroxide value" from Wikipedia, through the Wayback Machine, Archive Date: Apr. 24, 2017, 2 pages.
Pignitter, M. and Somoza, V.; Critical Evaluation of Methods for the Measurement of Oxidative Rancidity in Vegetable Oils. Journal of Food and Drug Analysis, vol. 20, No. 4, (2012), pp. 772-777. DOI:10.6227/jfda.2012200305.
Podolsky, D.K. Mucosal Immunity and Inflammation V. Innate mechanisms of mucosal defense and repair: the best offense is a good defense. The American Physiological Society, (1999), 277.3, G495-G499.
Search Report for United Arab Emirates Application No. P6002147/2021 filed on Nov. 24, 2021. 2 pages.
Second Notification of Office Action for Chinese Application No. 202080039535.3 on behalf of Alesco S.R.L Pharmanutra S.P.A. Issued on Nov. 6, 2024. 10 pages. Original + English translation.
Wallace, John L., Prostaglandins, NSAIDs, and Gastric Mucosal Protection: Why Doesn't the Stomach Digest Itself?, Physiol. Rev, 88, (2008), 1547-1565.
Wautier J. et al., "Pro- and Anti-Inflammatory Prostaglandins and Cytokines in Humans: A Mini Review" International Journal of Molecular Sciences, 24, Jun. 2023, pp. 1-13.
Werther, J.L., The gastric mucosal barrier. Mt Sinai J. Med., (Jan. 2000), 67 (1), 41-53. Abstract Only.
Wikipedia page for "Gastric mucosal barrier". Retrieved for Dec. 22, 2016 through the Wayback Machine.
World Health Organization, Eastern Mediterranean Region: Health promotion and disease prevention through population-based inter-

(56)                    References Cited

OTHER PUBLICATIONS ventions, including action to address social determinants and health inequality. Retrieved from the Wayback Machine archive for Apr. 9, 2019. 1 page.

World Health Organization, Eastern Mediterranean Region: Health promotion and disease prevention through population-based interventions, including action to address social determinants and health inequality. Retrieved on Jan. 13, 2025. 3 pages. www.emro.who.int/about-who/pulic-health-functions/health-promotion-disease-prevention.html.

Yang, Ines et al., Survival in hostile territory: the microbiota of the stomach. FEMS Microbiology Reviews, (Sep. 2013), 37(5): 736-761.

Notice of Allowance for U.S. Appl. No. 17/614,294, filed Nov. 24, 2021 on behalf of Alesco S.R.L. et al. Mail Date: Apr. 9, 2025 12 pages.

"Commission Implementing Regulation (EU) 2022/187 of 10 Feb. 10, 2022 authorising the placing on the market of cetylated fatty acids as a novel food under Regulation (EU) 2015/2283 of the European Parliament and of the Council, and amending Commission Implementing Regulation (EU) 2017/2470", Official Journal of the European Union, (Feb. 10, 2022) 6 pages.

Communication pursuant to Article 94(3) EPC for EP Application No. 20742895.4 filed Apr. 27, 2020 on behalf of Alesco S.r.l et al. Mailed on Apr. 8, 2024. 5 pages.

International Preliminary Report on Patentability for International Application No. PCT/IB2024/052210 filed on Mar. 7, 2024. Mailed on Sep. 9, 2025. 7 pages.

International Search Report and Written Opinion for International Application No. PCT/IB2024/052210 filed in Mar. 7, 2024 on behalf of Pharmanutra S.P.A. Mailed on Jun. 26, 2024. 10 pages.

International Specialty Products et al: "PVM/MA decadiene crosspolymer: a new thickener/stabilizer (International Specialty Products, Michael w Helioff)", Research Disclosure, Kenneth Mason Publications, Hampshire, UK, GB, vol. 343, No. 100, Nov. 1, 1992 (Nov. 1, 1992), XP007118376.

Motilva, V. et al.: "Mechanisms of increased gastric protection after NSAID-administration in rats consuming virgin olive oil diets", Jan. 29, 2008, vol. 3, No. 1, (Jan. 20, 2008). (Jan. 29, 2008), pp. e9-e16, XP022438813.

Musson, D.S. et al., "Bovine bone particulates containing bone anabolic factors as a potential xenogenic bone graft substitute", Journal of Orthopaedic Surgery and Research, (Feb. 20, 2019), 14:60. 11 pages.

"Rules for Conformity Assessment of Medical Devices according to Directive 93/42/EEC" (transposed by Italian legislative decree No. 46/97), (Feb. 14, 1997) 16 pages. RINA Services S.p.A.

* cited by examiner

PRODUCT C1

Rilascio PGE2/PGE2 release

ARNICA 5.5 CREAM

Rilascio PGE2/PGE2 release

COMPOSITIONS COMPRISING CETYLATED FATTY ACIDS FOR USE IN THE TREATMENT OF GASTRIC MUCOSA, DIABETES AND HIGH BLOOD GLUCOSE LEVELS

CROSS-REFERENCE TO RELATED APPLICATIONS

The present application is the U.S. National Stage of International Patent Application No. PCT/IB2020/055031 filed on May 27, 2020 which, in turn, claims priority to Italian Patent Application No. 102019000007329 filed on May 27, 2019.

The present invention relates to a composition comprising a mixture comprising alternatively, consisting of at least one cetylated fatty acid or a mixture of cetylated fatty acids and an antioxidant in reduced percentages by weight (for example, LIPOCET™), said composition being for use in methods for treatment of arthritis and of inflammatory joint and musculoskeletal pain. Furthermore, the present invention relates to a composition comprising a mixture comprising, or alternatively, consisting of at least one cetylated fatty acid or a mixture of cetylated fatty acids and, optionally, an antioxidant, said composition being for use in treatment methods for protecting the gastric mucosa and for regulating the blood glucose levels. Lastly, the present invention relates to a method for preparing said at least one cetylated fatty acid or mixture of cetylated fatty acids and for preparing compositions comprising said cetylated fatty acids and said antioxidant.

Compositions comprising mixtures of cetylated fatty acids and use thereof in the treatment of arthritis and joint inflammation are known in the prior art. For example, patent documents WO 2004/084829 A2 and WO 2017/029580 A1 describe compositions comprising cetylated fatty acids and, optionally, mixtures of tocophenols such as antioxidants at a % by weight comprised from 1% to 5%, with respect to the total weights of the compositions.

Document MAREN S. FRAGALA ET AL: *"Influences of a dietary supplement in combination with an exercise and diet regimen on adipocytokines and adiposity in women who are overweight"*, EUROPEAN JOURNAL OF APPLIED PHYSIOLOGY, SPRINGER, BERLIN, DE, vol. 105, no. 5) is a study aimed at investigating whether the administration of a mixture of modified cellulose and cetylated fatty acids (Trisynex® capsule Imagenetix) to a subject during an 8-week weight loss plan (with diet and physical exercise) causes a greater weight and fat loss to the subject as compared to the physical exercise alone and to the diet alone. Fasting serum insulin levels decrease, but there is no difference between the groups treated with and without cetylated fatty acids and modified cellulose.

International patent application no WO 00/64436 A1 relates to a composition for use in the treatment of pain, of diseases and of symptoms of primary biliary cirrhosis, autoimmune hepatitis or insulin-dependent diabetes, by means of administration of cetyl myristoleate (cetylated myristoleic acid). Example 1 describes enteric capsules containing 400 mg of cetyl myristoleate, 550 mg of extra virgin olive oil and 50 mg of lecithin.

International patent application no WO 2017/029580 A1 relates to a mixture comprising cetyl myristate (cetylated myristic acid) and cetyl oleate (cetylated oleic acid) for the treatment of cardiovascular disorders.

The technical problem addressed and solved by the present invention lies in providing compositions comprising improved cetylated fatty acids with respect to the known compositions, that are effective in the treatment of arthritis and inflammatory joint and musculoskeletal disorders, as well as in the protection of the gastric mucosa and in the regulation of blood glucose levels, free of adverse effects, well-tolerated, stable over time with respect to the action of the oxidising agents and, furthermore, economically advantageous to produce.

In order to overcome said technical problems, the present invention provides compositions (pharmaceutical compositions, medical device compositions, novel foods (food or food for special medical purpose (FSMP) or medical foods), dietary supplements or cosmetic compositions, in brief: compositions of the invention) comprising at least one cetylated fatty acid or a mixture of cetylated fatty acids and, optionally, at least one antioxidant (for example, LIPO-CET™).

The presence of the antioxidant makes the compositions of the invention stable over time, given that the titre of the active ingredient (cetylated fatty acids) remains almost unvaried over time, protecting the cetylated fatty acids from the action of the oxidising agents. Consequently, the presence of the antioxidant makes the compositions of the invention advantageous with respect to efficacy, transport, storage as well as preservation time and mode from the moment of first opening of the package containing the composition of the invention.

Furthermore, the presence of the antioxidant at a smaller % by weight with respect to the compositions based on cetylated fatty acids of the prior art makes the composition of the invention economically advantageous to produce on a large scale (i.e. use of a lower amount of antioxidant) and highly tolerated, for example, also when administered to paediatric subjects.

Said compositions of the invention (for example, LIPO-CET™) are capable of effectively and rapidly treating symptoms or disorders of the joint and/or muscular type such as the diseases, symptoms or disorders listed from (i) to (vi) hereinafter in the present description.

Furthermore, said compositions of the invention are capable (i.i) of protecting the gastric mucosa, (i.ii) of treating diabetes and (i.iii) of treating diseases and/or disorders other than diabetes deriving from or related with high blood glucose levels.

Lastly, the present invention provides a first method for preparing said at least one cetylated fatty acid or mixture of cetylated fatty acids and a second method for preparing said compositions of the invention comprising said at least one cetylated fatty acid or mixture of cetylated fatty acids (produced by means of said first method) and the antioxidant (for example, LIPOCET™).

Said methods are easy to apply and economically advantageous.

Furthermore, said first method—through the combined application of an inert gas flow over the entire duration of the step for forming the esters and a vacuum program in the chamber of the reactor only in the last part of the step for forming said ester—advantageously allows a complete conversion of acids and an excellent yield of the production of esters under simple and economical operating conditions.

Lastly, said first method ensures the production of cetylated fatty acids which are basically devoid of traces of catalyst and, thus, safe for health and well-tolerated by the subjects to whom they are administered.

These and other objects which will be clear from the detailed description that follows, are achieved by the compositions, by the mixtures and by the methods of the present invention thanks to the technical characteristics claimed in the attached claims.

DETAILED DESCRIPTION OF THE INVENTION

Following an intense research activity, the Applicant has developed innovative compositions, their uses in both therapeutic and non-therapeutic treatment methods and processes for their preparation, as reported in detail in the present description.

Figure 1:
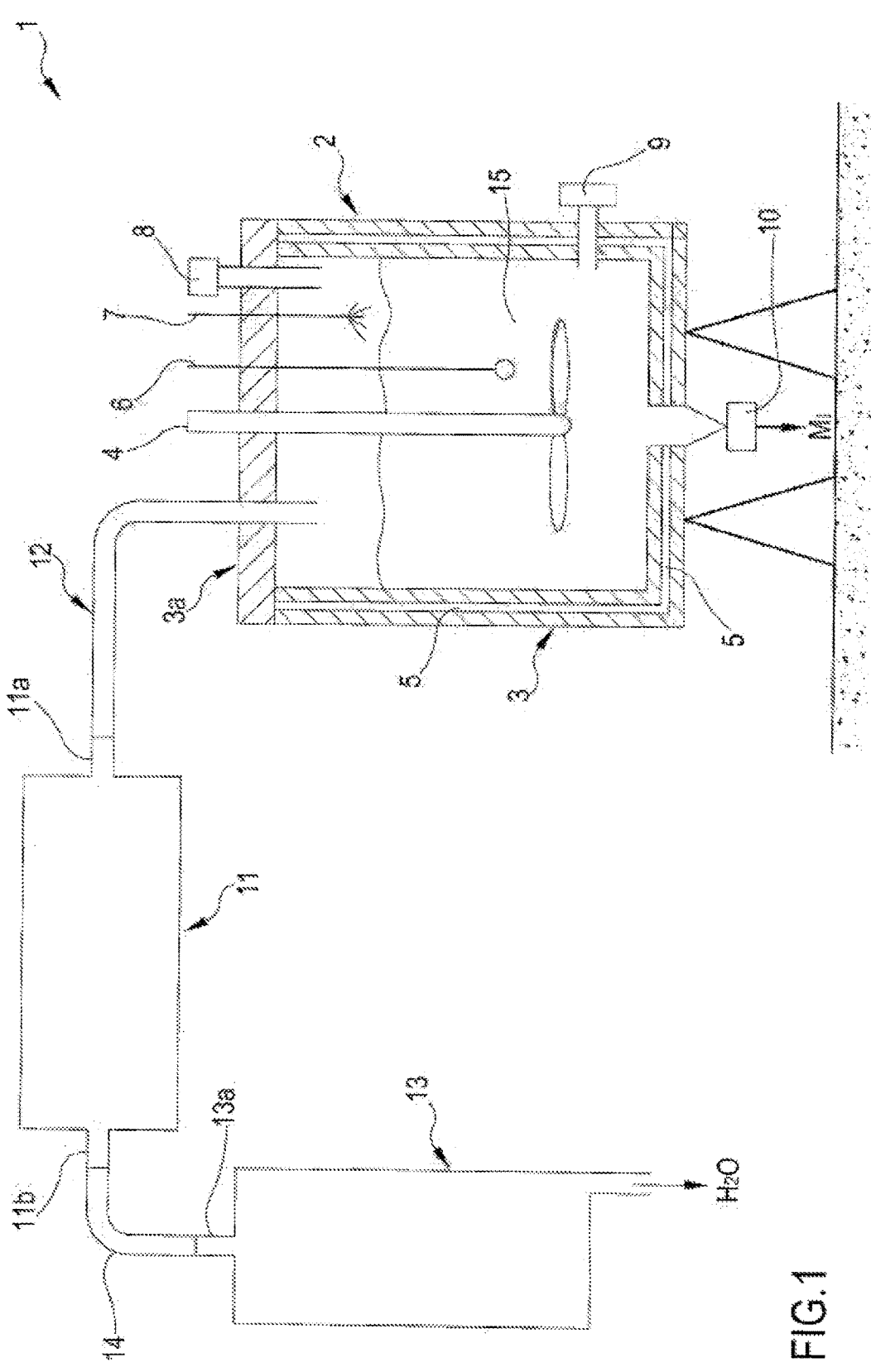
FIGS. 1, 2 and 3 show a plant for carrying out the first method for preparing (a) at least one cetylated fatty acid or a mixture of cetylated fatty acids.

Forming an object of the present invention is a composition (in short, composition of the invention) (for example, LIPOCET™ comprising (I) and, optionally, (II), wherein:

(I) is a mixture (in short, mixture of the invention) comprising or, alternatively, consisting of:

(a) at least one cetylated fatty acid (or a mixture of cetylated fatty acids), wherein said fatty acid has a carbon number comprised in the range from C6 to C21, preferably from C8 to C18, more preferably from C14 to C18, and it can be saturated or unsaturated, and, optionally, (b) at least one antioxidant at a % by weight comprised from 0.001% to 0.5% or from 0.001% to 0.4% or from 0.001% to 0.3% or from 0.001% to 0.2% or from 0.001% to 0.1% with respect to the total weight of the composition, preferably from 0.005% to 0.1%, more preferably from 0.01% to 0.08%; and (II) is at least one food or pharmaceutical grade additive and/or excipient.

The composition of the invention may be a pharmaceutical composition, a medical device composition, a novel food (food or beverage or food/beverage for special medical purpose (FSMP) or medical food) (for example, LIPO-CET™ or a dietary supplement or a composition for a novel food or a dietary supplement or a cosmetic composition.

In a preferred embodiment, the composition of the invention comprises the (I) mixture comprising or, alternatively, consisting of:

said (a) at least one cetylated fatty acid (or a mixture of cetylated fatty acids), wherein the fatty acid is C6-C21, C8-C18 or C14-C18 and it is saturated or unsaturated, and said (b) at least one antioxidant, at 0.001%-0.5% or from 0.001% to 0.4% or from 0.001% to 0.3% or from 0.001% to 0.2% or from 0.001% to 0.1% or 0.005%-0.1% or 0.01%-0.08% by weight with respect to the total weight of the composition.

Said (a) at least one cetylated fatty acid (or a mixture of cetylated fatty acids) is a fatty acid esterified with cetyl alcohol (1-hexadecanol, $CH_3(CH_2)_{15}OH$) or a mixture of fatty acids esterified with cetyl alcohol.

Preferably, the fatty acid of (a) at least one cetylated fatty acid is selected from among the group comprising or, alternatively, consisting of: lauric acid, myristic acid, palmitic acid, palmitoleic acid, stearic acid, oleic acid, linoleic acid, eicosanoic acid, and mixtures thereof; more preferably said (a) at least one cetylated fatty acid is a mixture of cetylated fatty acids comprising, or alternatively, consisting of a mixture of cetylated myristic acid and cetylated oleic acid; even more preferably said (a) at least one cetylated fatty acid is a mixture of cetylated fatty acids comprising or, alternatively, consisting of cetylated myristic acid, cetylated oleic acid, cetylated linoleic acid and cetylated palmitic acid.

According to an embodiment of the composition of the present invention, comprising (a), (b) and (c)—LIPOCET™ (according to any of the described embodiments), the fatty acid profile comprises or, alternatively, consists of:

(a1) myristic acid: from 30% to 55%, preferably from 35% to 50%, more preferably about 41%;

(a2) oleic acid: from 35% to 60%, preferably from 40% to 55%, more preferably about 46%;

(a3) linoleic acid: from 3% to 12%, preferably from 5% to 10%, more preferably about 8%;

(a4) palmitic acid: from 1% to 8%, preferably from 2% to 6%, more preferably about 3%;

(a5-a9) various fatty acids (not myristoleic acid): from 1% to 4%, preferably from 1.5% to 3%, more preferably about 1.8%; wherein the % are % by weight with respect to the total weight of the fatty acids from (a1 to (a9).

In an embodiment, said (a) comprises a mixture of cetylated myristic acid and cetylated oleic acid provided that said (a) does not comprise cetylated myristoleic acid, in particular, when the composition of the invention is for use in methods for treatment of arthritis and of inflammatory joint and musculoskeletal pain.

In a further embodiment, said (a) comprises a mixture of cetylated myristic acid and cetylated oleic acid which may also comprise cetylated myristoleic acid, in particular when the composition of the invention is for use in treatment methods for protecting the gastric mucosa and regulating blood glucose levels.

Myristic acid is tetradecanoic acid ($CH_3(CH_2)_{12}COOH$), a saturated fatty acid with 14 carbon atoms present in milk derivatives (butter, cream and cheese), coconut oil, palm seed oil and in some spices (nutmeg). The myristic acid used in the present invention may be, for example, selected from among those at 99% CAS 544-63-8 (EINECS 208-875-2) having a composition % (GLC): lauric acid C12:0 lower than or equal to 1; myristic acid C14:0 higher than or equal to 99%; palmitic acid C16:0 lower than or equal to 1.

Oleic acid is cis-9-octadecenoic acid ($CH_3(CH_2)_7CHCH$ $(CH_2)_7COOH$), a monounsaturated carboxylic acid with 18 carbon atoms and it is the most abundant constituent of most vegetable oils.

The oleic acid used in the present invention may be, for example, selected from among those having at least 78% in oleic acid CAS 112-80-1 (EINECS 204-007-1) with a % composition (GLC) for example: [lauric acid+myristic acid] C12:0+014:0 lower than or equal to 0.5; oleic acid C18:1 higher than or equal to 78%; linoleic acid C18:2 lower than or equal to 15 and other C18:3 lower than or equal to 1.

The cetyl alcohol (1-hexadecanol) used in the present invention may be, for example, selected from among those having CAS 36653-82-4 (EINECS 253-149-0).

Advantageously, when said (a) comprises or consists of a mixture of cetylated myristic acid and cetylated oleic acid, the mole ratio between the cetylated myristic acid and the cetylated oleic acid is comprised between 4:1 and 1:1, preferably it is comprised between 3:1 and 1.5:1, more preferably it is (2.0±0.2):1.

In a preferred embodiment, the composition of the invention comprises the (I) mixture comprising or, alternatively, consisting of:
- (a) a mixture of cetylated myristic acid and cetylated oleic acid, preferably at a mole ratio of 4:1-1:1 or 3:1-1.5:1 or preferably (2.0±0.2):1, and
- (b) at least one antioxidant, at 0.001%-0.5% by weight or from 0.001% to 0.3% or from 0.001% to 0.2% or from 0.001% to 0.1% or 0.005%-0.1% or preferably 0.01%-0.08%, with respect to the total weight of the composition.

The antioxidant comprised in the composition of the invention together with (a) and, optionally, with (c) may be any antioxidant considered—by the man skilled in the art—suitable for use in pharmaceutical compositions, medical device compositions, novel foods (foods), supplements or cosmetic compositions for the purposes reported in the present description.

Antioxidants are often added to foods predominantly containing fats, so as to delay the development of the rancidity that starts in the presence of oxygen. Natural antioxidants include flavonoids, polyphenols, ascorbic acid (vitamin C) and tocopherols (vitamin E). Synthetic antioxidants include butylhydroxyanisole (BHA), butylhydroxytoluene (BHT) and ethoxyquinoline.

Preferably, said (b) at least one antioxidant is selected from among the group comprising or, alternatively, consisting of: tert-butyl-hydroquinone (TBHQ), Aperoxid® TLA (as defined in the present invention), a tocopherol (for example tocopheryl acetate) or a mixture of tocopherols, a natural rosemary extract, wheat germ oil (*Triticum vulgare*), butylated hydroxytoluene and mixtures thereof, wheat germ oil (*Triticum vulgare*); more preferably (b) it is tert-butyl-hydroquinone (TBHQ).

Tert-butyl-hydroquinone (TBHQ or tertiary butylhydroquinone) is used in the food industry as a preservative for unsaturated vegetable oils and many edible animal fats. TBHQ is authorised as a food additive in the European Union with an acceptable daily intake (ADI) of 0.7 mg/kg of body weight and it is identified with the code E319.

Aperoxid® TLA (registered trademark) is the trade name of an antioxidant effective at combating the phenomenon of fat rancidity, used for example in the cosmetic field. Aperoxid® TLA is a mixture comprising tocopherol ((±)-α-tocopherol) 10-15%, lecithin>50%, ascorbyl palmitate 8-10% (an ester formed by ascorbic acid and palmitic acid creating a liposoluble form of vitamin C) and citric acid<1% (INCI NAME: lecithin, tocopherol ((±)-α-tocopherol), ascorbyl palmitate, citric acid; CAS NUMBER: 8002-43-5, 10191-41-0, 137-66-6, 77-92-9).

In a preferred embodiment, the composition of the invention comprises the (I) mixture comprising, or alternatively, consisting of:
- said (a) at least one cetylated fatty acid (or a mixture of cetylated fatty acids), wherein the fatty acid is C6-C21, C8-C18 or C14-C18 and it is saturated or unsaturated, and
- (b) tert-butyl-hydroquinone (TBHQ) at 0.001%-0.5% or from or from 0.001% to 0.3% or from 0.001% to 0.2% or from 0.001% to 0.1% or 0.005%-0.1% or 0.01%-0.08% by weight with respect to the total weight of the composition.

In a preferred embodiment, the composition of the invention comprises the (I) mixture comprising or, alternatively, consisting of:
- (a) a mixture of cetylated myristic acid and cetylated oleic acid, preferably at a mole ratio of 4:1-1:1 o 3:1-1.5:1 o (2.0±0.2):1, and
- (b) tert-butyl-hydroquinone (TBHQ), at 0.001%-0.5% or from 0.001% to 0.3% or from 0.001% to 0.2% or from 0.001% to 0.1% or 0.005%-0.1% or 0.01%-0.08% by weight with respect to the total weight of the composition.

In a more preferred embodiment, the composition of the invention comprises the (I) mixture comprising, or alternatively, consisting of:
- (a) a mixture of cetylated myristic acid and cetylated oleic acid at a mole ratio of 3:1-1.5:1, preferably (2.0±0.2):1, and
- (b) tert-butyl-hydroquinone (TBHQ) at 0.01%-0.08% by weight with respect to the total weight of the composition.

In a further embodiment, besides (a) and, optionally, (b), the (I) mixture of the invention further comprises (c) a vegetable oil.

Preferably said (c) vegetable oil is selected from among the group comprising or, alternatively, consisting of olive oil, sunflower oil, corn oil or mixtures thereof with high content of oleic acid, any vegetable oil with high content of oleic acid and mixtures thereof. Advantageously, (c) is olive oil. The content by weight of oleic acid and/or oleins in said oil is comprised from 55% to 95%, preferably from 60% to 90%, even more preferably from 65% to 85%, for example from 70% to 80%.

In a preferred embodiment, the (I) mixture of the invention comprises or, alternatively, consists of:
- said (a) at least one cetylated fatty acid (or a mixture of cetylated fatty acids), preferably a mixture of cetylated myristic acid and cetylated oleic acid, at a % by weight comprised from 50% to 90% with respect to the total weight of the composition, preferably from 60% to 85%, more preferably from 70% to 80%;
- said (b) at least one antioxidant, preferably tert-butyl-hydroquinone (TBHQ), at a % by weight comprised from 0.001% to 0.5% or from 0.001% to 0.3% or from 0.001% to 0.2% or from 0.001% to 0.1% with respect to the total weight of the composition, preferably from 0.005% to 0.1%, more preferably from 0.01% to 0.08%; and
- said (c) vegetable oil, preferably olive oil at a % by weight comprised from 9.5% to 50% with respect to the total weight of the composition, preferably from 14.5% to 40%, more preferably from 19.5% to 30%.

In a preferred embodiment, the (I) mixture of the invention comprises, or alternatively, consists of:
- (a) a mixture of cetylated myristic acid and cetylated oleic acid at a mole ratio of 4:1-1:1 or 3:1-1.5:1, preferably (2.0±0.2):1; preferably at a % by weight comprised from 60% to 85% with respect to the total weight of the composition, preferably from 70% to 80%;
- (b) tert-butyl-hydroquinone (TBHQ) at a % by weight comprised from 0.005% to 0.1% with respect to the total weight of the composition, preferably from 0.01% to 0.08%; and
- (c) olive oil at a % by weight comprised from 14.5% to 40% with respect to the total weight of the composition, preferably from 19.5% to 30%.

In a more preferred embodiment, the (I) mixture of the invention comprises, or alternatively, consists of:

(a) a mixture of cetylated myristic acid and cetylated oleic acid at a mole ratio of (2.0±0.2):1 and at a % by weight comprised from 70% to 80%;

(b) a tert-butyl-hydroquinone (TBHQ) at a % by weight comprised from 0.01% to 0.08% with respect to the total weight of the composition; and (c) an olive oil at a % by weight comprised from 19.5% to 30% with respect to the total weight of the composition.

Forming an object of the present invention are the compositions of the invention reported in the present description (for example, LIPOCET™) comprising: (I) the mixture of the invention, comprising or consisting of (a) and (b) and, optionally, (c) (as defined above), and, optionally, (II) at least one food or pharmaceutical grade additive and/or excipient, said compositions being for use as medicament when administered, at a therapeutically effective amount, to a subject in need.

Forming an object of the present invention are compositions of the invention (for example, LIPOCET™) comprising (a) and (b) and, optionally, (c) (according to all embodiments described in the present description) for use in a method for preventive and/or curative and/or symptomatic treatment of diseases, symptoms or disorders such as (i) rheumatoid arthritis of inflammatory and non-inflammatory origin, in particular osteoarthritis; (ii) joint inflammatory conditions other than rheumatoid arthritis; (iii) psoriasis, lupus, periodontal diseases or cardiovascular or heart diseases; (iv) post-traumatic osteoarticular and musculoskeletal diseases including sports-related traumas, for example pubalgia or athletic pubalgia (pubalgia refers to a chronic pain of the abdomen and groin); (v) degenerative joint diseases, preferably osteoarthritis, gonarthrosis, coxarthrosis, and/or (vi) tendon and muscle-related inflammatory/traumatic conditions, when administered to a subject in need.

Preferably, the compositions of the invention for use in a method for treatment of diseases or disorders from (i) to (vi) as identified above comprise the (I) mixture comprising or, alternatively consisting of:

(a) a mixture of cetylated myristic acid and cetylated oleic acid at a mole ratio of 3:1-1.5:1, preferably (2.0±0.2):1, and (b) tert-butyl-hydroquinone (TBHQ) at 0.01%-0.08% by weight with respect to the total weight of the composition.

Preferably, the compositions of the invention for use in a method for treatment of diseases or disorders from (i) to (vi) as identified above comprise the (I) mixture comprising or, alternatively consisting of:

(a) a mixture of cetylated myristic acid and cetylated oleic acid at a mole ratio of (2.0±0.2):1 and at a % by weight comprised from 70% to 80%;

(b) tert-butyl-hydroquinone (TBHQ) at a % by weight comprised from 0.01% to 0.08% with respect to the total weight of the composition; and (c) olive oil at a % by weight comprised from 19.5% and 30% with respect to the total weight of the composition.

Said compositions of the invention for use in a method for treatment of diseases, symptoms or disorders listed from (i) to (vi), as defined above, are administered to said subject preferably through the topical or transdermal route; more preferably through the topical route. Advantageously, the cetylated fatty acids from (a1) to (a7) comprised in the mixture (a) have a molecular weight comprised from 420 Da to 510 Da. This molecular weight range allows the mixture (a), and thus, the composition of the present invention, to effectively overcome the dermal barrier (skin) facilitating the absorption thereof through the topical route.

Alternatively, said compositions of the invention for use in a method for treatment of diseases, symptoms or disorders listed from (i) to (vi), as defined above, are administered to said subject preferably through the oral route.

Forming an object of the present invention are the compositions of the invention (for example, LIPOCET™ comprising (a) and (b) and, optionally, (c) (according to all embodiments described in the present description) for use in a method for preventive and/or curative and/or symptomatic treatment of (i.i) symptoms and/or disorders deriving from or related with damage to the gastric mucosa (treatment for protecting the gastric mucosa), (i.ii) diabetes and disorders or symptoms deriving from or related with diabetes, (i.iii) diseases and/or disorders other than diabetes deriving from or related with high blood glucose levels, when administered to a subject in need.

Said (i.i) symptoms or disorders deriving from or related with the damage of the gastric mucosa (protection of the gastric mucosa) are selected from among the group comprising or, alternatively, consisting of: gastric ulcers, gastroesophageal reflux (GERD), heartburn.

Advantageously, effective and lasting protection of the gastric mucosa exerted by the use of the composition of the present invention in rats was observed in vivo in rats. Gastric mucosa is known to exert a barrier effect and it consists of a mucosal layer of about 0.2 mm which covers the mucous membrane of the stomach. The purpose of this barrier is to protect the gastric epithelium from the damaging action of the HCl produced by the parietal cells of the stomach. It derives from the production—by the gastric surface cells—of high molecular weight (thus very viscous) mucoprotein droplets and from the production of bicarbonate.

Therefore, forming an object of the present invention is a composition (see Table 2 or Samples 2-6) for use in a method for the (preventive and/or curative) treatment of a disorder or symptom deriving from or—related with the damage of the gastric mucosa selected from among the group comprising or, alternatively, consisting of: gastric ulcers, gastroesophageal reflux (GERD), heartburn.

Said (i.iii) diseases and/or disorders other than diabetes deriving from or related with high blood glucose levels are selected from among the group comprising or, alternatively, consisting of: hyperglycaemia, chronic liver diseases, obesity.

Advantageously, it was found that through the in vivo administration to rats of a composition of the present invention, for example the composition of Sample 4, at high doses, for example at doses higher than 1,600 mg/Kg, the glucose levels in the blood of the treated rats are statistically significantly reduced.

Therefore, forming an object of the present invention is a composition (see Table 2 or Samples 2-6) for use in a method for treatment of diabetes or of a disease and/or disorder other than diabetes deriving from, or related with, high blood glucose levels, such as in the case of hyperglycaemia, chronic liver diseases and obesity.

Said compositions of the invention for use in a method for treatment of diseases, symptoms or disorders listed from (i.i) to (i.iii), as defined above, are administered to said subject preferably through the oral route.

Preferably, the compositions of the invention for use in a method for treatment of diseases or disorders from (i.i) to (i.iii) as identified above comprise the (I) mixture comprising or, alternatively, consisting of:

(a) a mixture of cetylated myristic acid and cetylated oleic acid, preferably at a mole ratio of 4:1-1:1 or 3:1-1.5:1 or preferably (2.0±0.2):1, and (b) tert-butyl-hydroquinone (TBHQ) at 0.01%-0.08% by weight with respect to the total weight of the composition.

The compositions of the invention may be formulated in a liquid form, such as solution, biphasic liquid system or emulsion, suspension, syrup, spray, ointment, oil or beverage or, alternatively, in a semisolid form, such as gel, soft-gel, cream, foam, or, alternatively, in a solid form, such as powder, spray powder (spray drying), granules, micro-granules, flakes, aggregates, buccal soluble sticks, tablets, effervescent tablets, capsules, suppositories, bars or food and equivalent forms known to the man skilled in the art. For example, the compositions of the invention can be formulated for oral use as capsules comprising (a) a mixture of cetylated fatty acids according to the invention, (b) at least one antioxidant at the % according to the invention and excipients such as, for example, gelatine, glycerol and/or preservatives (for example, LIPOCET™). In an embodiment, the composition is in the form of 300 mg capsules of bovine gelatine.

Advantageously, when the composition of the invention is for oral use, it is formulated in solid or liquid form, more preferably in the form of capsules or oil or powder or spray powder (spray drying) or spray liquid or beverage or food.

Advantageously, when the composition of the invention is for topical use, it is formulated in semisolid form, more preferably in the form of cream or gel.

Advantageously, when the composition of the invention is for transdermal use, it is formulated in form suitable to be applied by means of a patch.

Forming an object of the present invention are methods for treatment of diseases, symptoms or disorders listed above from (i) to (vi), preferably by means of administration through the topical or transdermal or oral route, or, alternatively, for the treatment of diseases, symptoms or disorders listed above from (i.i) to (i.iii), preferably by means of oral administration, to a subject in need of an effective amount of one of the compositions of the invention comprising (a) or (a) and (b) or (a) and (b) and (c) described in the present description.

The appropriate assay of the composition of the present invention will depend, for example, on the condition to be treated/prevented, on the severity and course of the condition, on the fact that the composition is administered for preventive or therapeutic purposes, prior therapy, the patient's clinical history and response to the composition and at the discretion of the treating physician.

When the composition of the invention is administered through the topical route, the amount of the administered composition is of about from 1 mg/kg to 15 mg/kg of body weight of said subject per day, preferably 3-10 mg/kg, more preferably 5-8 mg/kg. Furthermore, the composition of the invention, for example a cream or gel, is applied through the topical route on an area comprised in the range from 1 cm to 25 cm in diameter on the area to be treated, depending on the anatomical area in question (for example, fingers: 3 cm, back: 20 cm).

When the composition of the invention is administered through the oral route, the amount of the administered composition is of about from 100 mg/kg to 5000 mg/kg of body weight of said subject per day, preferably from 200 mg/kg to 4500 mg/kg, more preferably from 300 mg/kg to 4,000 mg/kg. The composition of the invention is suitably administered to the subject all at once or on several treatments.

The composition may be administered as a single treatment or in combination with other compositions or therapies (i.e. as coadjuvant) useful in the preventive and/or curative and/or symptomatic treatment of the diseases, symptoms and/or disorders listed from (i) to (vi) and/or listed from (i.i) to (i.iii) as described in the present description.

Forming an object of the present invention is the non-therapeutic use of the composition of the invention comprising (a) or (a) and (b) or (a) and (b) and (c) for the protection of the gastric mucosa, wherein said composition is preferably formulated for oral use.

The composition of the invention protects the gastric mucosa so as to prevent the damaging thereof and thus the onset of disorders related with the gastric region such as, for example, gastric ulcers, gastroesophageal reflux (GERD), heartburn.

In the context of the present invention, the expression "subjects" is used to indicate human subjects or animal subjects (e.g. pets, such as dogs or cats or other mammals). Preferably, the compositions of the invention are for use in treatment methods for human subjects.

The expression "treatment method" in the context of the present invention is used to indicate an action, comprising the administration of a substance, or mixture of substances or combination thereof, with the aim of eliminating, reducing/decreasing or preventing a pathology or disease and its symptoms or disorders.

The expression "medical device" in the context of the present invention is used according to the meaning laid down by the Italian Legislative Decree no 46, dated 24 Feb. 1997 (or according to the new Medical Devices Regulation (EU) 2017/745 (MDR)), i.e. it indicates a substance or another product, used alone or in combination, designated by the manufacturer to be used in humans for the diagnosis, prevention, control, therapy or attenuation of a disease, the product not exercising the main action, in or on the human body, for which it is designated, neither using pharmacological or immunology means nor by means of a metabolic process but the function thereof can be coadjuvated by such means.

The compositions of the invention optionally comprise (II) at least one food or pharmaceutical grade additive and/or excipient, such as a substance devoid of therapeutic activity suitable for pharmaceutical or food use, such as, for example, diluents, solvents (e.g. water, glycerine, ethyl alcohol), solubilizers, thickeners, sweeteners, anti-caking agents, flavour enhancers, colourants, lubricants, surfactants, antimicrobials, antioxidants, preservatives, pH stabilizing buffers, acidifiers and all auxiliary substances known to the man skilled in the art.

Besides said (a), (b), and, optionally, (c), the compositions of the invention may further comprise other active components such as, for example, anti-inflammatories, probiotics, antacids, products for the treatment of joint and/or muscle-related disorders, vitamins of group B and E, mineral salts, pain killers, folic acid or folates, menthol, glucosamine, chondroitin, methylsulfonylmethane (MSM), essential oils.

Unless specified otherwise, the indication that a composition "comprises" one or more components or substances means that other components or substances can be present besides the one, or the ones, indicated specifically.

Unless specified otherwise, the expression composition comprises a component at an amount "comprised in a range from x to y" is used to indicate that said component may be present in the composition at all the amounts present in said range, even though not specified, extremes of the range comprised.

Forming an object of the present invention is a first method for preparing said (a) at least one cetylated fatty acid (or a mixture of cetylated fatty acids) as defined in the present description comprising the steps of (FIG. 1):

(I) placing at least one fatty acid, cetyl alcohol and a catalyst, preferably a metal catalyst, at contact in a chamber 3 of a reactor 2 in the absence of solvent, to obtain a reaction mixture 15; followed by (II) saturating the container 3 with an inert gas, bringing the container 3 to a pressure P1 of about 1 atmosphere, applying a flow of said inert gas through said chamber 3, preferably a flow comprised from 5 m³/h to 0.05 m³/h, more preferably 0.5 m³/h; followed by (III) applying a first heating ramp to said reaction mixture 15 up to reaching a temperature T1 comprised from 120° C. to 200° C., preferably from 145° C. to 175° C., more preferably at 160° C., at a pressure P1 of about 1 atmosphere and in the presence of the inert gas flow to initiate an esterification reaction with initial formation of said cetylated fatty acid or mixture of cetylated fatty acids and esterification water; followed by (IV) keeping said reaction mixture 15 under stirring at said temperature T1 and pressure P1 for a period of time comprised from 10 minutes to 2 hours, preferably from 30 minutes to 1.5 hours, more preferably for 1 hour; followed by (V) applying a second heating ramp to said reaction mixture 15 up to reaching a temperature T2 comprised from 201° C. to 260° C., preferably from 210° C. to 240° C., more preferably at 220° C., at a pressure P1 of about 1 atmosphere and in the presence of the inert gas flow to continue the esterification reaction with further formation of said cetylated fatty acid or mixture of cetylated fatty acids and esterification water; followed by (VI) keeping said reaction mixture 15 under stirring at said temperature T2 and pressure P1 and in the presence of the inert gas flow for a period of time comprised from 4 hours to 12 hours, preferably from 6 hours to 10 hours, more preferably for 8 hours; preferably up to reaching an acidity value of the reaction mixture 15 measured using the AOCS Official Method Cd 3d-63, stable over time and comprised from 5 mgKOH/g to 8 mgKOH/g; followed by (VII) applying a vacuum program in the chamber 3 reducing the reaction pressure up to reaching a reduced pressure P2 comprised from 100 mbar to 10 mbar, preferably from 80 mbar to 30 mbar, more preferably 50 mbar; followed by (VIII) keeping said reaction mixture 15 under stirring at said reduced pressure P2 and in the presence of the inert gas flow for a period of time comprised from 30 minutes to 4 hours, preferably from 1 hour to 2 hours, more preferably for 2 hours; preferably up to reaching an acidity value of the reaction mixture 15 measured using the AOCS Official Method Cd 3d-63, comprised from 4.5 mgKOH/g to 3.5 mgKOH/g, preferably 4 mgKOH/g, to obtain complete formation of said at least one unrefined cetylated fatty acid or mixture of unrefined cetylated fatty acids (MI).

By means of the combined application of an inert gas flow for part or the entire duration of the step for forming the esters and a vacuum program in the reactor chamber only in the last part of the step for forming said ester, said first method advantageously allows the removal of the esterification water and the complete conversion of fatty acids into esters with excellent yield. Said first method is simple to apply and economically advantageous, since it is not necessary to apply a vacuum program for the entire duration of the esterification reaction.

In an embodiment (FR1) of said first method, said at least one fatty acid is selected from among the group comprising or, alternatively, consisting of lauric acid, myristic acid, palmitic acid, palmitoleic acid, stearic acid, oleic acid, linoleic acid, eicosanoic acid and mixtures thereof; preferably selected from among myristic acid, oleic acid and a mixture of myristic acid and oleic acid; more preferably a mixture of myristic acid and oleic acid, even more preferably a mixture of myristic acid and oleic acid provided that myristoleic acid is not comprised in said mixture.

In an embodiment (FR2) of said first method, said inert gas flow is applied using the blowing means 7 positioned in the volume portion of the chamber 3 overlying the reaction mixture 15 (FIG. 1).

Figure 2:
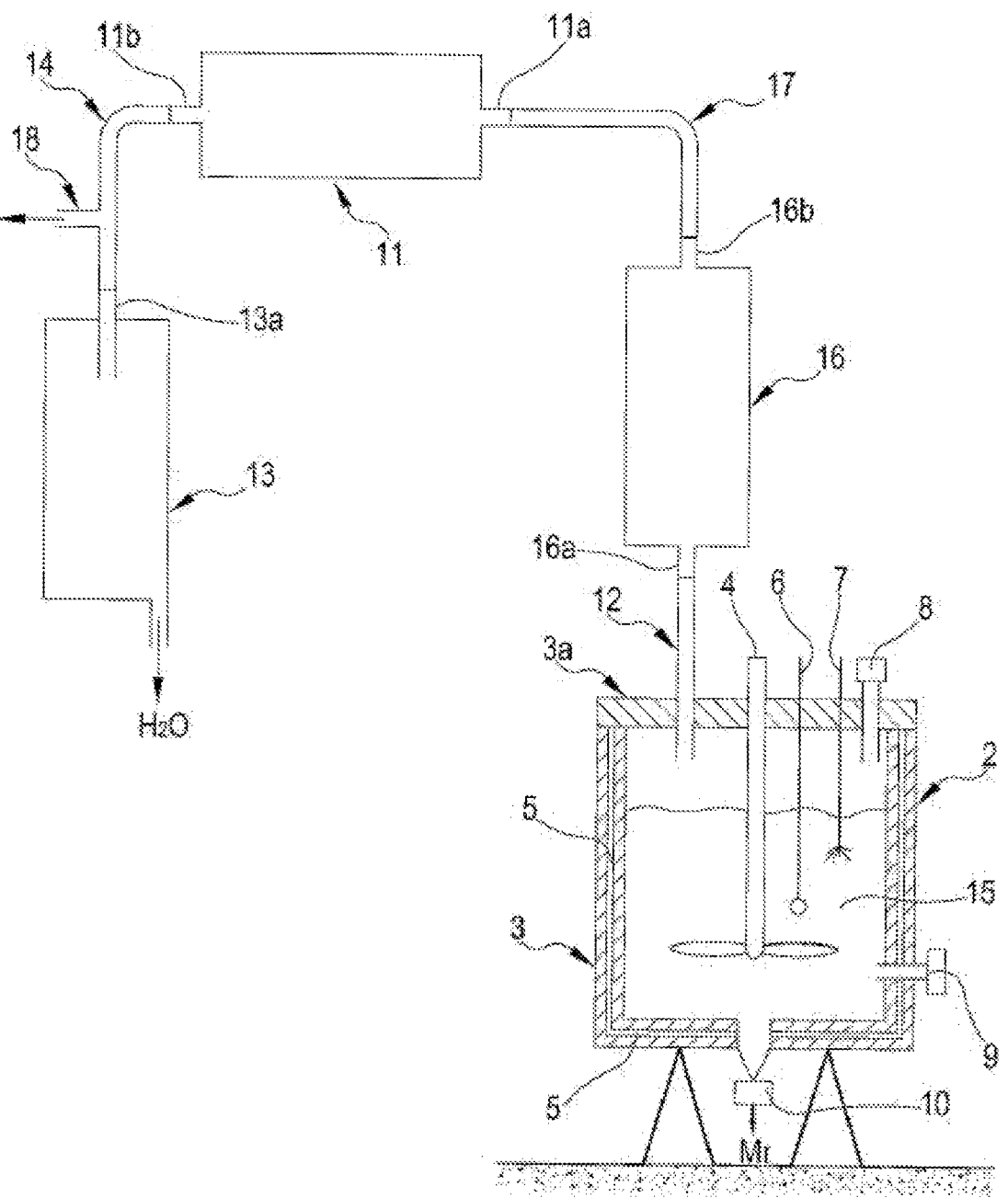
Figure 3:
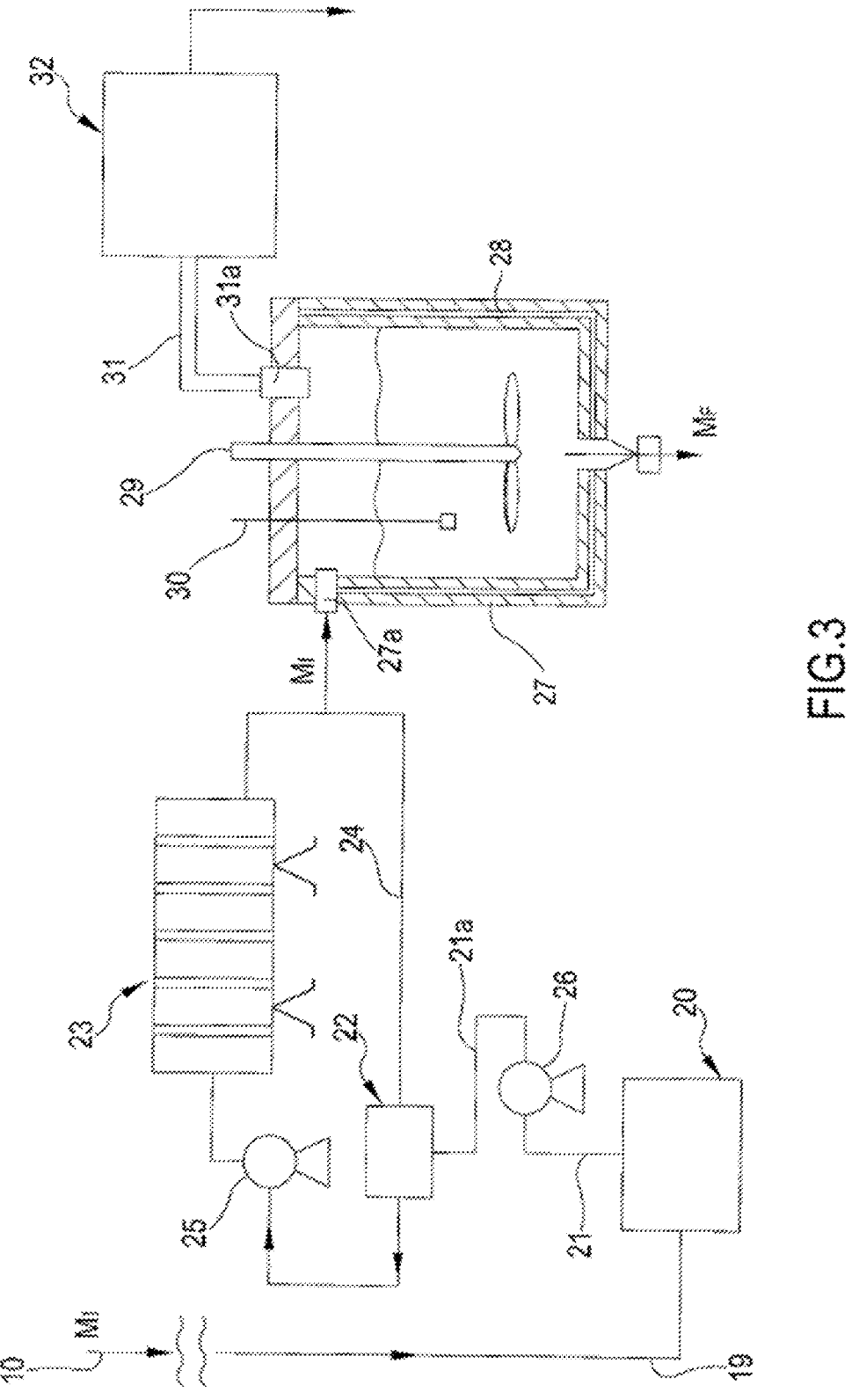

In an embodiment (FR3) of said first method, the esterification water, drawn out of the chamber 3 during the esterification reaction by applying the inert gas flow and the vacuum program described above, is condensed in a horizontal condenser 11 and collected in a container 13 after flowing through a vertical condenser 16 (FIGS. 2 and 3).

In an embodiment (FR4) of said first method, said horizontal condenser 11 is kept at a temperature comprised from 10° C. to 40° C. and it is connected to said container 3 by means of a vertical condenser 16 which is kept at a temperature comprised from 70° C. to 90° C. (FIG. 3).

In an embodiment (FR5) of said first method, besides steps (I)-(VIII), said first method further comprises the step (IX) of filtering said at least one unrefined cetylated fatty acid or mixture of unrefined cetylated fatty acids (MI) obtained from step (VIII) on bleaching earth and/or filtering earth in a filter press 23 (FIG. 3), to obtain at least one filtered cetylated fatty acid or a mixture of filtered cetylated fatty acids (Mf) wherein the metal catalyst is substantially absent or present at an amount less than or equal to 2% by weight, preferably at an amount comprised from 0.01% to 1.5%, even more preferably at an amount comprised from 0.05% to 1%, for example 0.5% by weight, with respect to the weight of said filtered cetylated fatty acid or mixture of filtered cetylated fatty acids (Mf).

The metal catalyst (zero oxidation state metal), preferably metal zinc, is preferably used in powder form, preferably powdered metal zinc. The amount of catalyst added is comprised in the range from 0.01% to 0.5% by weight with respect to the total weight of the reaction reagents (i.e. fatty acid or mixture of fatty acids+cetyl alcohol), preferably from 0.05% to 0.25% by weight, even more preferably 0.1% by weight.

In an embodiment (FR6) of said first method, besides steps (I)-(IX), said first method further comprises the step (X) (deodorisation step) of treating said at least one filtered cetylated fatty acid or mixture of filtered cetylated fatty acids (Mf) in a reactor 27 (FIG. 3) at a temperature T3 comprised from 150° C. to 200° C., preferably from 165° C. to 180° C., more preferably at 180° C., and a reduced pressure P3 comprised from 1 mbar to 20 mbar, preferably from 3 mbar to 5 mbar, in the presence of water vapour flow for a period of time comprised from 1 hour to 5 hours, preferably from 2 hours to 3 hours, to obtain at least one refined cetylated fatty acid or mixture of refined cetylated fatty acids (Mf).

Forming an object of the present invention is a second method for preparing a composition of the invention comprising said (a) at least one cetylated fatty acid (or mixture of cetylated fatty acids) as defined in the present description, wherein said second method comprises the step (XI) of mixing said at least one filtered cetylated fatty acid (Mf), obtainable according to the embodiment FR5 in combination with any one of embodiments FR1-FR4 or, alternatively, said at least one refined cetylated fatty acid (MF), obtainable according to the embodiment FR6 in combination with any one of embodiments FR1-FR5, with (b) at least one antioxidant (as defined in the present invention), wherein said (b) at least one antioxidant is mixed at a % by weight comprised from 0.001% to 0.5% or from 0.001% to 0.4% or from 0.001% to 0.3% or from 0.001% to 0.2% or from 0.001% to 0.1% with respect to the total weight of the composition (composition of the invention), preferably from 0.005% to 0.1%, more preferably from 0.01% to 0.08%.

In a preferred embodiment, said second method for preparing a composition of the invention comprises the step of mixing said at least one filtered cetylated fatty acid (Mf) or at least one refined cetylated fatty acid (MF) comprising or, alternatively, consisting of a mixture of cetylated myristic acid and cetylated oleic acid, preferably at a mole ratio of 4:1-1:1 or 3:1-1.5:1 or (2.0±0.2):1 or about 1:1, and wherein said (b) at least one antioxidant is tert-butyl-hydroquinone (TBHQ) at a % by weight comprised from 0.001% to 0.5% or from 0.001% to 0.4% or from 0.001% to 0.3% or from 0.001% to 0.2% or from 0.001% to 0.1% with respect to the total weight of the composition, preferably from 0.005% to 0.1%, more preferably from 0.01% to 0.08%.

In an embodiment, said at least one filtered cetylated fatty acid (or mixture of cetylated fatty acids) (Mf), preferably a mixture of filtered cetylated myristic acid and cetylated oleic acid, before being subjected to the deodorisation step (X), is added with said (c) a vegetable oil (as defined in the present invention), preferably olive oil or corn oil.

In an embodiment, before the deodorisation step (X), said at least one filtered cetylated fatty acid (Mf), preferably a mixture of filtered cetylated myristic acid and cetylated oleic acid, is subjected to the step (XII) of adding said (Mf) with said (c) a vegetable oil, preferably olive oil or corn oil, to form a mixture comprising (Mf) and (c) which is subsequently subjected to the deodorisation step (X).

In a preferred embodiment, deodorisation step (X) of the first method to obtain at least one refined cetylated fatty acid (MF), preferably a mixture of refined cetylated myristic acid and cetylated oleic acid, and the step (XI) of mixing said at least one refined cetylated fatty acid (MF) with at least one antioxidant, preferably TBHQ, of the second method and, optionally, the step (XII) of adding the at least one filtered cetylated fatty acid (Mf) with (c) the vegetable oil, are carried out in the same reactor.

Basically, the method of the present invention can be summarised schematically with the following embodiments:
1) MI (step I-VIII)→Mf (step IX)→MF (step X)+(b) (step (XI))+(c) (step (XII));
2) MI (step I-VIII)→Mf (step IX)+(c) (step XII)→MF (step X)+(b) (step (XI)),
3) MI (step I-VIII)→Mf (step IX)+(b) (step XI)→MF (step X)+(c) (step (XII));

Said (a) at least one cetylated fatty acid (or a mixture of cetylated fatty acids) is a fatty acid esterified with a cetyl alcohol (1-hexadecanol, CH3(CH2)15OH).

Preferably, the fatty acid of said (a) at least one cetylated fatty acid is selected from among the group comprising or, alternatively, consisting of: (a1) myristic acid, (a2) oleic acid, (a3) linoleic acid, (a4) palmitic acid, (a5) lauric acid, (a6) palmitoleic acid, (a7) stearic acid, (a8) eicosanoic acid, (a9) eicosenoic acid and mixtures thereof; more preferably said (a) at least one cetylated fatty acid is a mixture of cetylated fatty acids comprising, or alternatively, consisting of cetylated myristic acid, cetylated oleic acid, cetylated linoleic acid and cetylated palmitic acid; even more preferably said (a) comprises, or alternatively, consists of a mixture of a cetylated myristic acid and a cetylated oleic acid.

According to an embodiment of the composition of the present invention, comprising (a), (b) (at least one antioxidant) and (c) (for example, LIPOCET™) (according to any of the described embodiments), the fatty acid profile comprises or, alternatively, consists of:
(a1) myristic acid: from 30% to 55%, preferably from 35% to 50%, more preferably from 40% to 45%; for example 41%, or 42%, or 43%, 44%;
(a2) oleic acid: from 35% to 60%, preferably from 40% to 55%, more preferably from 45% to 50%; for example 46%, or 47%, or 48%, or 49%;
(a3) linoleic acid: from 3% to 12%, preferably from 5% to 10%, more preferably from 6% to 9%; for example 7%, or 8%, or 8.5%;
(a4) palmitic acid: from 1% to 8%, preferably from 2% to 6%, more preferably from 3% to 5%; for example 3.5%, or 4%, or 4.5%.

Furthermore, said (a)+(b)+(c) may comprise together with one or more said (a1) to (a4):
(a5) lauric acid from 0.1% to 0.3%, for example 0.2%;
(a6) palmitoleic acid from 0.3% to 0.5%; for example 0.4%;
(a7) stearic acid from 0.7% to 0.9%, for example 0.8%;
(a8) eicosanoic acid from 0.05% to 0.15%, for example 0.1%;
(a9) eicosenoic acid from 0.2% to 0.4%, for example 0.3%.

The total amount of said from (a5) to (a9) is preferably comprised from 1% to 4%, preferably comprised from 1.5% to 3%; even more preferably from 2% to 2.5%, for example 1.8% by weight.

The chromatographic separation of said mixture (a)+(b)+(c) leads to obtaining a wax fraction from (a1) to (a9) (at % by weight) comprised from 60% to 80%, preferably from 65% to 75%; the remaining part being the glyceride fraction. The chain length distribution in said wax fraction is of the type: 30 carbon atoms from 60% to 70%; 32 carbon atoms from 1% to 3%; and 34 carbon atoms from 25% to 35%. In said wax fraction, the amount of myristic acid is comprised from 60% to 70%, whereas that of oleic acid is comprised from 25% to 35% by weight.

Embodiments of the mixture (a)+(b)+(c) are reported hereinafter:

Sample 2: composition according to the invention comprising:
a mixture of: cetylated myristic acid and cetylated oleic acid, at a myristic:oleic mole ratio of about 2.1:1 (about 75% by weight with respect to the total weight of the sample);
olive oil or corn oil (about 25% by weight with respect to the total weight of the sample);
tert-butyl-hydroquinone (TBHQ) (0.02% by weight with respect to the total weight of the sample) and, optional, excipients and/or additives.

Sample 3: composition according to the invention comprising:
a mixture mainly comprising cetylated myristic acid and cetylated oleic acid, at a myristic:oleic mole ratio of about 2.1:1 (about 75% by weight with respect to the total weight of the sample);
olive oil or corn oil (about 25% by weight with respect to the total weight of the sample),
Aperoxid® TLA (0.05% by weight with respect to the total weight of the sample) and, optional,
excipients and/or additives.
Sample 4, a composition comprising:
a mixture mainly comprising cetylated myristic acid and cetylated oleic acid, at a myristic:oleic mole ratio of about 2.1:1 (about 75% by weight with respect to the total weight of the sample),
olive oil or corn oil (about 25% by weight with respect to the total weight of the sample),
mixture of tocopherols or tocopheryl acetate (0.001-0.3%) and, optional,
excipients and/or additives.
Sample 5: Composition according to the invention:
a mixture of: (a1)+(a2)+(a3), at a mole ratio of (a1):(a2): (a3)=4:4:1 (about 80% by weight, with respect to the total weight of the sample);
an olive or corn oil (about 20% by weight, with respect to the total weight of the sample);
a mixture of tocopheryl acetate and wheat germ oil (*Triticum vulgare*) at a by weight ratio of 1:25; and, optional,
excipients and/or additives.
Sample 6: Composition according to the invention:
a mixture of: (a1)+(a2)+(a3)+(a4), at a mole ratio of (a1):(a2):(a3):(a4)=4:4:1:0.5 (about 85% by weight, with respect to the total weight of the sample);
an olive or corn oil (about 15% by weight, with respect to the total weight of the sample);
a mixture of tocopheryl acetate and wheat germ oil (*Triticum vulgare*) at a by weight ratio of 1:25; and, optional,
excipients and/or additives.

Embodiments (An) according to a first object of the present invention are reported below:

An1. A composition comprising (I) and, optionally, (II), wherein:
(I) is a mixture comprising or, alternatively, consisting of:
(a) at least one cetylated fatty acid wherein said fatty acid is a saturated or unsaturated fatty acid having a number of carbons comprised in the range from C6 to C21, and
(b) at least one antioxidant at a % by weight comprised in the range from 0.001% to 0.5% with respect to the total weight of the composition; and (II) is at least one food or pharmaceutical grade additive and/or excipient.
An2. The composition according to An1, wherein said fatty acid of (a) at least one cetylated fatty acid is selected from among the group comprising, or alternatively, consisting of: myristic acid, oleic acid and a mixture thereof;
preferably (a) comprises or, alternatively, consists of a mixture of cetylated myristic acid and cetylated oleic acid.
An3. The composition according to An1 or An2, wherein said (b) at least one antioxidant is selected from among the group comprising, or alternatively, consisting of: tert-butyl-hydroquinone (TBHQ), a mixture comprising tocopherol, lecithin, ascorbyl palmitate and citric acid (Aperoxid® TLA), a mixture of tocopherols and a natural rosemary extract; preferably (b) it is tert-butyl-hydroquinone (TBHQ).

An4. The composition according to any one of An1 to An3, wherein said (b) at least one antioxidant is present at a % by weight comprised in the range from 0.005% to 0.1% with respect to the total weight of the composition, preferably from 0.01% to 0.08%.
An5. The composition according to any one of An1 to An4, wherein
said (a) comprises, or alternatively, consists of a mixture of cetylated myristic acid and cetylated oleic acid, wherein the mole ratio between said cetylated myristic acid and cetylated oleic acid is comprised in a range from 4:1 to 1:1, preferably from 3:1 to 1.5:1, more preferably it is (2.0±0.2):1; and
said (b) is tert-butyl-hydroquinone (TBHQ) and it is present at a % by weight comprised in the range from 0.001% to 0.5% with respect to the total weight of the composition, preferably from 0.005% to 0.1%, more preferably from 0.01% to 0.08%.
An6. The composition according to any one of An1 to An5, wherein besides (a) and (b) said composition further comprises (c) a vegetable oil; preferably said vegetable oil is selected from among the group comprising or, alternatively, consisting of olive oil and sunflower oil with high oleic content.
An7. The composition according to any one of An1 to An6, wherein said composition comprises:
said (a) at least one cetylated fatty acid, preferably a mixture of cetylated myristic acid and cetylated oleic acid, at a % by weight comprised in the range from 50% to 90% with respect to the total weight of the composition, preferably from 60% to 85%, more preferably from 70% to 80%;
said (b) antioxidant, preferably tert-butyl-hydroquinone (TBHQ), at a % by weight comprised in the range from 0.001% to 0.5% with respect to the total weight of the composition, preferably from 0.005% and 0.1%, more preferably from 0.01% to 0.08%; and
said (c) vegetable oil, preferably olive oil, at a % by weight comprised in the range from 9.5% to 50% with respect to the total weight of the composition, preferably from 14.5% to 40%, more preferably from 19.5% to 30%.
An8. The composition according to any one of An1 to An7, wherein said composition is for use as medicament.
An9. The composition for use according to An8, wherein said composition is for use in a method for preventive and/or curative and/or symptomatic treatment of (i) rheumatoid arthritis of inflammatory and non-inflammatory origin, in particular osteoarthritis; (ii) joint inflammatory conditions other than rheumatoid arthritis; (iii) psoriasis, lupus, periodontal diseases or cardiovascular or heart diseases; (iv) post-traumatic osteoarticular and musculoskeletal diseases including sports-related traumas; (v) degenerative joint diseases, preferably arthrosis, gonarthrosis, coxarthrosis, and/or (vi) tendon and muscle-related inflammatory/traumatic conditions, by means of administration to a subject in need.
An10. The composition for use according to An8 or An9, wherein said composition is formulated for topical or transdermal use; preferably for topical use.

Embodiments (Bn) according to a second object of the present invention are reported below:

17

Bn1. A composition comprising:
(I) a mixture comprising or, alternatively, consisting of (a) at least one cetylated fatty acid, and, optionally,
(II) at least one pharmaceutical or food grade additive and/or excipient,
wherein said composition is for use in a method for preventive and/or curative treatment of
(i.i) a disorder or symptom deriving from and/or related with damaging the gastric mucosa selected from among the group comprising or, alternatively, consisting of: gastric ulcers, gastroesophageal reflux (GERD), heartburn;
(i.ii) diabetes;
(i.iii) a disease and/or disorder other than diabetes deriving from or related with high blood glucose levels selected from among the group comprising or, alternatively, consisting of: hyperglycaemia, chronic liver diseases, obesity;
by administering to a subject in need.
Bn2. The composition for use according to Bn1, wherein said fatty acid of (a) at least one cetylated fatty acid is selected from among the group comprising or, alternatively, consisting of: lauric acid, myristic acid, palmitic acid, palmitoleic acid, stearic acid, oleic acid, linoleic acid, eicosanoic acid, and mixtures thereof; preferably myristic acid, oleic acid or cetylated myristic acid and cetylated oleic acid.
Bn3. The composition for use according to Bn2, wherein in said mixture of cetylated myristic acid and cetylated oleic acid the mole ratio between cetylated myristic acid and cetylated oleic acid is comprised in the range from 4:1 to 1:1, preferably from 3:1 to 1.5:1, more preferably it is (2.0±0.2):1.
Bn4. The composition for use according to any one of Bn1 to Bn3, wherein said (I) mixture, comprising said (a), further comprises (b) at least one antioxidant.
Bn5. The composition for use according to Bn4, wherein said (b) at least one antioxidant is selected from among the group comprising or, alternatively, consisting of tert-butyl hydroquinone (TBHQ), a mixture comprising tocopherol, lecithin, ascorbyl palmitate and citric acid (Aperoxid® TLA), a mixture of tocopherols and a natural rosemary extract; preferably (b) it is tert-butyl-hydroquinone (TBHQ).
Bn6. The composition for use according to Bn4 or Bn5, wherein said (b) at least one antioxidant is present at a % by weight comprised in the range from 0.001% to 0.5% with respect to the total weight of the composition, preferably from 0.005% to 0.1%, more preferably from 0.01% to 0.08%.
Bn7. The composition for use according to any one of Bn1 to Bn6, wherein said (I) mixture comprises or, alternatively, consists of:
said mixture of cetylated myristic acid and cetylated oleic acid;
preferably wherein the mole ratio between the cetylated myristic acid and cetylated oleic acid is comprised in the range from 4:1 to 1:1, preferably it is comprised from 3:1 to 1.5:1, more preferably it is (2.0±0.2):1; and
said (b) tert-butyl-hydroquinone (TBHQ);
preferably wherein (b) it is present at a % by weight comprised in the range from 0.001% to 0.5% with respect to the total weight of the composition, preferably from 0,005% to 0.1%, more preferably from 0.01% to 0.08%.
Bn8. The composition according to any one of Bn1 to Bn7, wherein besides (a) and (b), said composition further comprises (c) a vegetable oil; preferably, said vegetable oil is selected from among the group comprising or, alternatively, consisting of olive oil, sunflower oil with a high oleic content and mixtures thereof.
Bn9. The composition for use according to any one of Bn1 to Bn8, wherein said composition is formulated for oral use.
Bn10. The composition for use according to any one of Bn1 to Bn9, wherein said composition is for use as a coadjuvant of one or more further compositions for use in the preventive and/or curative treatment of (i.i), (i.ii) or (i.iii).
Embodiments (Cn) according to a third object of the present invention are reported below:
Cn1. A method for preparing (a) at least one cetylated fatty acid or a mixture of cetylated fatty acids comprising the steps of:
(I) placing at contact at least one fatty acid, cetyl alcohol and a metal catalyst in a chamber (3) of a reactor (2) in absence of solvent, to obtain a reaction mixture (15); followed by
(II) saturating the container (3) using an inert gas bringing the container (3) to a pressure P1 of about 1 atmosphere, applying a flow of said inert gas through said chamber (3); followed by
(III) applying a first heating ramp to said reaction mixture (15) up to reaching a temperature T1 comprised from 120° C. to 200° C. at a pressure P1 of about 1 atmosphere and in the presence of the inert gas flow to initiate an esterification reaction with initial formation of said cetylated fatty acid or mixture of cetylated fatty acids and esterification water; followed by
(IV) keeping said reaction mixture (15) under stirring at said temperature T1 and pressure P1 for a period of time comprised from 10 minutes to 2 hours; followed by
(V) applying a second heating ramp to said reaction mixture (15) up to reaching a temperature T2 comprised from 201° C. to 260° C. at a pressure P1 of about 1 atmosphere and in the presence of the inert gas flow to continue the esterification reaction with further formation of said cetylated fatty acid or mixture of cetylated fatty acids and esterification water; followed by
(VI) keeping said reaction mixture (15) under stirring at said temperature T2 and pressure P1 and in the presence of the inert gas flow for a period of time comprised from 4 hours to 12 hours;
(VII) applying a vacuum program in the chamber (3) which reduces the reaction pressure up to reaching a reduced pressure P2 comprised from 100 mbar to 10 mbar;
(VIII) keeping said reaction mixture (15) under stirring at said reduced pressure P2 and in the presence of the inert gas flow for a period of time comprised from 30 minutes and 4 hours to obtain complete formation of said at least one unrefined cetylated fatty acid or mixture of unrefined cetylated fatty acids (MI).
Cn2. The method according to Cn1, wherein said step (VI) of keeping said reaction mixture (15) under stirring at said temperature T2 and pressure P1 and in the presence of the inert gas flow for a period of time comprised from 6 hours to 12 hours is carried out up to reaching an acidity value of the reaction mixture (15) measured using the AOCS Official Method Cd 3d-63 stable over time and comprised from 5 mgKOH/g to 8 mgKOH/g; and said step (VIII) of keeping said reaction mixture (15) under stirring at said reduced pressure P2 and in the presence of the inert gas flow for a period of time comprised from 30 minutes to 4 hours up to reaching an acidity value of the reaction mixture (15) measured using the AOCS Official Method Cd 3d-63 comprised from 4.5 mgKOH/g to 3.5 mgKOH/g to obtain complete formation of said at least one unrefined cetylated fatty acid or mixture of unrefined cetylated fatty acids (MI).

Cn3. The method according to Cn1 or Cn2, wherein said at least one fatty acid is selected from among the group comprising or, alternatively, consisting of lauric acid, myristic acid, palmitic acid, palmitoleic acid, stearic acid, oleic acid, linoleic acid, eicosanoic acid, and mixtures thereof;

preferably selected from among myristic acid, oleic acid and a mixture of myristic acid and oleic acid.

Cn4. The method according to any one of Cn1 to Cn3, wherein said inert gas flow is applied by means of the blowing means (7) positioned in the volume portion of the chamber (3) overlying the reaction mixture (15).

Cn5. The method according to any one of Cn1 to Cn4, wherein the esterification water, drawn out of the chamber (3) during the esterification reaction by applying the inert gas flow and the vacuum program, is condensed in a horizontal condenser (11) and collected in a container (13) after flowing through a vertical condenser (16).

Cn6. The method according to any one of Cn1 to Cn5, wherein said method further comprises the step (IX) (filtration step) of filtering said at least one unrefined cetylated fatty acid (MI) obtained from step (VIII) on bleaching earth and/or filtering earth in a filter press (23), to obtain at least one filtered cetylated fatty acid (Mf) wherein the metal catalyst is absent or present at an amount less than 2% by weight with respect to the weight of said filtered cetylated fatty acid or mixture of filtered cetylated fatty acids (Mf).

Cn7. The method according to any one of Cn1 to Cn6, wherein said method further comprises, subsequently to the step (IX), step (X) (deodorisation step) of treating said at least one filtered cetylated fatty acid (Mf) in a reactor (27) at a temperature T3 comprised from 150° C. to 200° C. and a reduced pressure P3 comprised from 1 mbar to 20 mbar in the presence of a water vapour flow for a period of time comprised from 1 hour to 5 hours to obtain at least one refined cetylated fatty acid (MF).

Cn8. A method for preparing a composition comprising said (a) at least one cetylated fatty acid comprising the step of mixing said at least one filtered cetylated fatty acid (Mf) obtainable according to any one of the embodiments Cn1 to Cn6 or, alternatively, said at least one refined cetylated fatty acid (MF) obtainable according to any of the embodiments Cn1 to Cn7 with at least one antioxidant, wherein said at least one antioxidant is mixed at a % by weight comprised from 0.001% to 0.5% with respect to the total weight of the composition, preferably from 0.005% to 0.1%, more preferably from 0.01% to 0.08%.

Cn9. The method for preparing a composition according to Cn8, wherein said at least one filtered cetylated fatty acid (Mf) or at least one refined cetylated fatty acid (MF) comprises or, alternatively, consists of a mixture of cetylated myristic acid and cetylated oleic acid, and wherein said at least one antioxidant is tert-butyl hydroquinone (TBHQ).

Cn10. The method for preparing a composition according to Cn8 or Cn9, wherein before step (X), said at least one filtered cetylated fatty acid (Mf) obtained from step (IX), preferably a mixture of filtered cetylated myristic acid and cetylated oleic acid, is subjected to a step (XII) of adding said at least one filtered cetylated fatty acid (Mf) with a vegetable oil, preferably olive oil, to form a mixture comprising (Mf) and vegetable oil which is subsequently subjected to step (X).

Experimental Part 1

In experimental part 1 the stability of compositions of the invention comprising or not comprising an antioxidant was analysed. All the compositions reported in Table 2 and Samples 1, 2 and 3 were tested using the same method described hereinafter. In particular, the tests conducted on Samples 2 and 3 (according to the invention) and on Sample 1 (comparative sample) are reported by way of non-limiting example. This is because the stability results obtained with the compositions reported in Table 2 are mutually comparable to those of Samples 2 and 3, thanks to the presence of at least one antioxidant in the tested compositions.

Material

Premise: the % by weight of Samples 1, 2 and 3 refer to the total weight of the sample.

Sample 1: (comparative composition) composition comprising:
- a mixture mainly comprising cetylated myristic acid and cetylated oleic acid, at a myristic:oleic mole ratio of about 2.1:1 (about 75% by weight with respect to the total weight of the sample),
- olive oil or corn oil (about 25% by weight with respect to the total weight of the sample).

Sample 1 does not comprise antioxidants.

Sample 2: composition according to the invention comprising:
- a mixture mainly comprising cetylated myristic acid and cetylated oleic acid, at a myristic:oleic mole ratio of about 2.1:1 (about 75% by weight with respect to the total weight of the sample);
- olive oil or corn oil (about 25% by weight with respect to the total weight of the sample);
- tert-butyl hydroquinone (TBHQ) (0.02% by weight with respect to the total weight of the sample) and, optional,
- excipients and/or additives.

Sample 3: composition according to the invention comprising:
- a mixture mainly comprising cetylated myristic acid and cetylated oleic acid, at a myristic:oleic mole ratio of about 2.1:1 (about 75% by weight with respect to the total weight of the sample);
- olive oil or corn oil (about 25% by weight with respect to the total weight of the sample),
- Aperoxid® TLA (0.05% by weight with respect to the total weight of the sample) and, optional,
- excipients and/or additives.

Methodology

After a time T0, samples 1, 2 and 3 were stored at a controlled temperature of 18° C. Approximately every 40-45 days (i.e. at times T1, T2, T3 and T4), a sample was taken from each sample and the peroxide value (PV) and the Kreiss' test were determined.

Peroxide Values

The peroxide value (PV) was determined in a standard way according to the ISO3960 method (fourth edition 2007-07-15, corrected version 2009-05-15, prepared by the Technical Committee ISO/TC 34/SC), as known to the man skilled in the art.

Said test is a classical analytical chemistry method for determining the degree of rancidity of a food oil. The test quantitatively determines the peroxide value (PV), which is an index of the amount of primary autoxidation products of fatty acids.

The method provides for (briefly): the oil sample is dissolved in isooctane and glacial acetic acid (glacial acetic acid:isooctane=6:4 v/v) and potassium iodide is added. Iodine released from the peroxides is determined iodometrically (visually) with a starch indicator and a standard solution of sodium thiosulphate ($Na_2S_2O_3$ 0.01 N). The titration endpoint is determined iodometrically (visually).

The PV is expressed as mEq of oxygen per kg of oil.

Given that determination of the peroxide value (PV) is a highly empirical procedure, ISO3960:2007 set the mass of the sample at 5 g for PV greater than 1 and at 10 g for PV less than or equal to 1, and limited the applicability of this method to animal and vegetable fats and oils with peroxide values from 0 mEq to 30 mEq of active oxygen per kilogram.

—Kreiss' Test

The Kreiss' test is performed in a standard manner, as known to the man skilled in the art.

The Kreiss' test is a chemical test for qualitatively determining the degree of rancidity of a food oil. The test is used to detect the secondary products of the autoxidation of fatty acids.

As a matter of fact, the organoleptic properties of rancid and rancidifying fats are significantly correlated to the presence of carbonyl products formed by interaction between oxygen and unsaturated fatty acids.

Phloroglucinol (1,3,5-triphenol or symmetrical triphenol) is a chemical compound of the triphenol group, of the brute formula C6H6O3 which crystallises from the aqueous solutions thereof as dihydrate (C6H6O3·2H2O).

The Kreiss' test is based on the condensation reaction between carbonyl compounds (arising from fat rancidity) with phloroglucinol in the presence of HCl which gives rise to a red compound. This is a qualitative method and the result is considered positive when the colouration of the lower layer is more intense than a 0.0012% solution of $KMnO_4$ and negative when the opposite occurs.

Kreiss' Test Method 1. 10 ml of oil and 10 ml of concentrated HCl are stirred for 30 seconds.
2. 10 ml of reagent are added: 0.1% solution of phloroglucinol in ethyl ether and kept under stirring for a further 30 seconds.

After stratification, the colouration of the lower acid layer is examined:

negative reaction⇒brownish or faded colouration;
positive reaction⇒pink or red colouration (rancid oil).

Results

As reported in Table 1, samples 2 and 3 (compositions according to the present invention comprising an antioxidant) show at times T3 (i.e. after about 150 days) and T4 (i.e. after about 210 days) a peroxide value (PV) significantly lower than in sample 1 (composition in the absence of antioxidant). Furthermore, samples 2 and 3 are negative to Kreiss' test at times T3 and T4, while sample 1 is positive.

TABLE 1

| | | T0 | T1 after 30 days | T2 after 60 days | T3 after 60 days | T4 after 60 days |
|---|---|---|---|---|---|---|
| Sample 1 (in the absence of antioxidant) | P. V. (MEq Active oxygen/kg) | nd | 6.51 | 6.92 | 24.38 | 27.47 |
| | Kreiss' test | nd | negative | negative | positive | positive |
| Sample 2 (with antioxidant) | P. V. (MEq Active oxygen/kg) | nd | 5.62 | 5.4 | 6.55 | 4.39 |
| | Kreiss' test | nd | negative | negative | negative | negative |
| Sample 3 (with antioxidant) | P. V. (MEq Active oxygen/kg) | nd | 4.77 | 6.47 | 8.64 | 5.34 |
| | Kreiss' test | nd | negative | negative | negative | negative |

Experimental Part 2

An in vivo toxicity study of a compound according to the invention (Sample 4) was conducted in experimental part 2.

In vivo study: 14-day oral toxicity study, in Crl CD Sprague Dawley (SD) rats, of a compound according to the invention.

Compound Subject of Study:

Sample 4, a composition comprising:

a mixture mainly comprising cetylated myristic acid and cetylated oleic acid, at a myristic:oleic mole ratio of about 2.1:1 (about 75% by weight with respect to the total weight of the sample), olive oil or corn oil (about 25% by weight with respect to the total weight of the sample), at least one antioxidant at percentage by weight from 0.001% to 0.3% (with respect to the total weight of the sample), for example a mixture of tocopherols or tocopheryl acetate.

Test system: 60 Sprague Dawley rats (30 males and 30 females) seven weeks old at the start of treatment.

Size group: 5 males and 5 females of rats/group.

Assay levels: 0-1600-1900-2200-2600-4500 mg/kg of body weight.

Volume of administration: 10 ml/kg of body weight.

Treatment mixtures: prepared weekly and kept at 4° C.

Treatment plan: every day for 14 consecutive days.

Treatment procedure: daily volume of administration divided into two equal secondary fractions given to each fasting rat with a 60-minute interval.

OBSERVATIONS: Mortality (daily); Clinical signs (daily); Body weight (twice a week); Food consumption (twice a week); Haematology (sacrifice); Clinical chemistry (sacrifice); Urinalysis (sacrifice); Gross pathology; Histology (if necessary).

STATISTICS: the data were analysed using ANOVA, followed by Post hoc Dunnett tests with the JMP statistical detection software.

Results:

A statistically significant dose-dependent difference related to glucose level was recorded in the high-dose tested group, which was significantly lower ($p<0.05$) with respect to the control group (reverse relationship between the administered compound dose of the invention and the glucose level). Surprisingly, it was found that by administering to rats, for example the composition of Sample 4, at the highest doses, the blood glucose levels are statistically significantly reduced in the blood of the treated rats. Thanks to this result, the compositions of the present invention find valid application/use in a method for the treatment of subjects suffering from diabetes or from a disease and/or disorder other than diabetes deriving from, or related with high blood glucose levels, like in the case of hyperglycaemia, chronic liver diseases and obesity.

Complete haematology revealed no treatment-related differences between the groups and found no clinical signs over the 14-day treatment period.

No abnormalities were recorded in the leukocyte differential count and in the urinalysis between the experimental groups.

Body weight increase and food intake are comparable in all groups and no behavioural abnormalities were observed throughout the rat treatment period.

No anomalies were recorded at necropsy level: all organs and tissues of the various systems showed normal appearance, size, colour and position.

Thus, Sample 4 (compound according to the invention) is well tolerated at all the tested doses and the blood glucose levels are statistically significantly lower in the group of high-dose rats (inverse dose-effect relationship).

Surprisingly, an effective and durable gastric mucosal protection was visually observed through the present in vivo study in rats. Gastric mucosa is known to exert a barrier effect and it consists of a mucosal layer of about 0.2 mm which covers the mucous membrane of the stomach. The purpose of this barrier is to protect the gastric epithelium from the damaging action of the HCl produced by the parietal cells of the stomach. It derives from the production—by the gastric surface cells—of high molecular weight (thus very viscous) mucoprotein droplets and from the production of bicarbonate. Therefore, the compositions of the present invention (see Table 2), for example Sample 2-6 find valid application/use in a method for the (preventive and/or curative) treatment of a disorder or symptom deriving from or—related with the damage of the gastric mucosa selected from among the group comprising or, alternatively, consisting of: gastric ulcers, gastroesophageal reflux (GERD), heartburn.

The in vivo toxicity study reported above was repeated at 90 days. The results are comparable to those obtained at 14 days. In particular, at the dose of 4500 mg/Kg of body weight of the tested rats (maximum dose which did not give toxicity effects) it is surprisingly observed that the tested rats maintained and preserved a good thyroid function without alteration of food and social behaviour.

Experimental Part 3

In vitro efficacy study—in vitro evaluation of the anti-inflammatory activity of products according to the present invention and comparative products on cell culture.

1. STUDY DESIGN

The study described in experimental part 3 was intended to evaluate—in an in vitro system—the ability of the tested products to modulate inflammatory mechanisms induced in human tenocyte cultures (ZEN BIO TEN-F, Lot #TENM012214F). The study of anti-inflammatory activity was conducted through the assay—using the ELISA method—of some inflammation markers, in particular proinflammatory cytokines IL6, prostaglandin E2 (PGE2) and leukotriene C4 (LTC4), the latter products of cyclooxygenase and lipoxygenase—the main enzymes involved in the inflammatory cascade from arachidonic acid—activity respectively.

2. PRODUCTS TESTED

CREAM products Cn (compositions according to the invention, according to Table 2, C1-C6): concentration 0.050%, 0.025% and 0.010%.
ARNICA 5.5% CREAM: concentration 0.070%, 0.035% and 0.014%.
GLUCOSAMINE 5.5% CREAM: concentration 0.070%, 0.035% and 0.014%.

The tested products are all creams based on glycerine and/or glyceryl monostearate.

The products according to the invention (Cream Cn products) tested in said in vitro anti-inflammatory activity evaluation study have the following compositions reported in Table 2 (from C1 to C6). All the C1-C6 products according to the present invention gave similar experimental results. Thus, only the data of the Cream product C1, representing products C2-C6, will be reported hereinafter.

TABLE 2

| INGREDIENTS | amt % w/w Range | amt % w/w C1 | amt % w/w C2 | amt % w/w C3 | amt % w/w C4 | amt % w/w C5 | amt % w/w C6 | activity — |
|---|---|---|---|---|---|---|---|---|
| Purified water | 70-80 | 77.5 | 77.5 | 80 | 80 | 80 | 80 | solvent |
| Mixture of cetylated fatty acids in vegetable oil (*) | 3-10 | 7.5 | 7.5 | 8 | 8 | 8 | 8 | lubricant |
| Antioxidants: at least one selected from among the group A-G | 0.001-0.03 | — | — | — | — | — | — | — |
| A: Butylated hydroxytoluene | — | 0.005 | — | — | — | — | — | Antioxidant |
| B: Tocopheryl acetate | — | 0.008 | 0.01 | — | — | — | — | Antioxidant |
| C: Tert-butyl-hydroquinone (TBHQ) | — | — | 0.05 | 0.05 | — | 0.05 | — | Antioxidant |
| D: Aperoxid ® TLA | — | — | — | — | 0.05 | — | — | Antioxidant |
| E: Rosemary extract | — | — | — | — | — | — | 0.01 | Antioxidant |

TABLE 2-continued

| INGREDIENTS | amt % w/w Range | amt % w/w C1 | amt % w/w C2 | amt % w/w C3 | amt % w/w C4 | amt % w/w C5 | amt % w/w C6 | activity — |
|---|---|---|---|---|---|---|---|---|
| F: Mixture of tocopherols | — | — | — | — | 0.01 | 0.05 | — | Antioxidant |
| G: Wheat germ oil (Triticum vulgare) | — | 0.025 | 0.01 | — | — | — | 0.05 | Antioxidant |
| Glycerine (Vegetable glycerine) | 1-10 | 3 | 3 | 3 | 3 | 3 | 3 | Humectant |
| Glyceryl monostearate | 0.5-5 | 2.5 | 2.5 | 2.5 | 2.5 | 2.5 | 2.5 | Emulsifier |
| Butylene glycol | 0.5-5 | 1.5 | 1.5 | 1.5 | 1.5 | 1.5 | 1.5 | Humectant |
| Additives and/or excipients | q.s. 100 | q.s. 100 | q.s. 100 | q.s. 100 | q.s. 100 | q.s. 100 | q.s. 100 | — |

(*) Mixture of cetylated fatty acids in vegetable oil (olive oil or corn oil or sunflower oil) comprises or, alternatively, consists of cetylated:

(a1) myristic acid: from 30% to 55%, preferably from 35% to 50%, more preferably about 41%;

(a2) oleic acid: from 35% to 60%, preferably from 40% to 55%, more preferably about 46%;

(a3) linoleic acid: from 3% to 12%, preferably from 5% to 10%, more preferably about 8%;

(a4) palmitic acid: from 1% to 8%, preferably from 2% to 6%, more preferably about 3%;

(a5-a9) various fatty acids (not myristoleic acid): from 1% to 4%, preferably from 1.5% to 3%, more preferably about 1.8%; wherein the % are % by weight with respect to the total weight of said mixture of cetylated fatty acids; wherein the weight ratio (a):(c)=4:1, 3:1, 2:1, or 1:1.

Before being subjected to the efficacy test, the samples were prepared in culture medium, starting from the following ratios: 0.05 g diluted in 1 ml with culture medium. Subsequent dilutions in culture medium.

The products were subjected to preliminary cytotoxicity test aimed at selecting the most suitable concentrations for the final test. After evaluating the results of the cytotoxicity test, the above reported concentrations were selected for conducting the anti-inflammatory activity study.

3. METHOD

For the test, human tenocyte cultures (ZEN BIO TEN-F, Lot #TENM012214F) were treated for 48 hours with interleukin-1 beta (IL-1β, 10 ng/ml—dose selected following a range finding test), an agent involved in the tendinopathy inflammatory conditions, and simultaneously with the products tested at 3 concentrations, selected from among the non-cytotoxic ones following a preliminary cytotoxicity test. At the end of the monitored experimental period, the levels of the inflammatory markers of interest in the culture media were measured using ELISA. Results were compared with negative control cultures (untreated, CTR−) and positive control cultures (treated with IL-1β, CTR+).

In summary, the experimental protocol provided for the assay of three pro-inflammatory markers (IL6, LTC4 and PGE2) in:

untreated cell cultures (negative control, CTR−);

cell cultures in which an inflammation event was experimentally induced (positive control, CTR+);

cell cultures in which an inflammation event was experimentally induced and simultaneously treated with the products subjected to the test.

4. ASSAY OF THE INFLAMMATION MARKERS (IL6, PGE2 AND LTC4)

The culture media of the controls and of the cells treated with the products subjected to the test (paragraph 2) were used for the determination of the inflammatory markers IL6, PGE2 and LTC4 using the ELISA method.

Commercially available kits—which exploit the competitive binding of an antigen (the cytokine of interest in this case) with the primary antibody thereof—were used for this purpose. The immune complex (antigen-antibody) is in turn recognised by a secondary antibody conjugated to a peroxidase. The addition of the peroxidase substrate produces a colorimetric reaction with intensity proportional to the amount of immune complexes present and thus to the amount of bound cytokine. Quantitative determination exploits a calibration curve constructed with known and increasing concentrations of standard cytokine.

5. RESULTS

The following tables and charts show the results obtained in the present study.

The results are reported as the amount of cytokine released in the culture medium during the experimental period (mean value±std.dev.) and as a mean % variation as compared to the controls.

Results for IL6 Assay

Figure 4A:
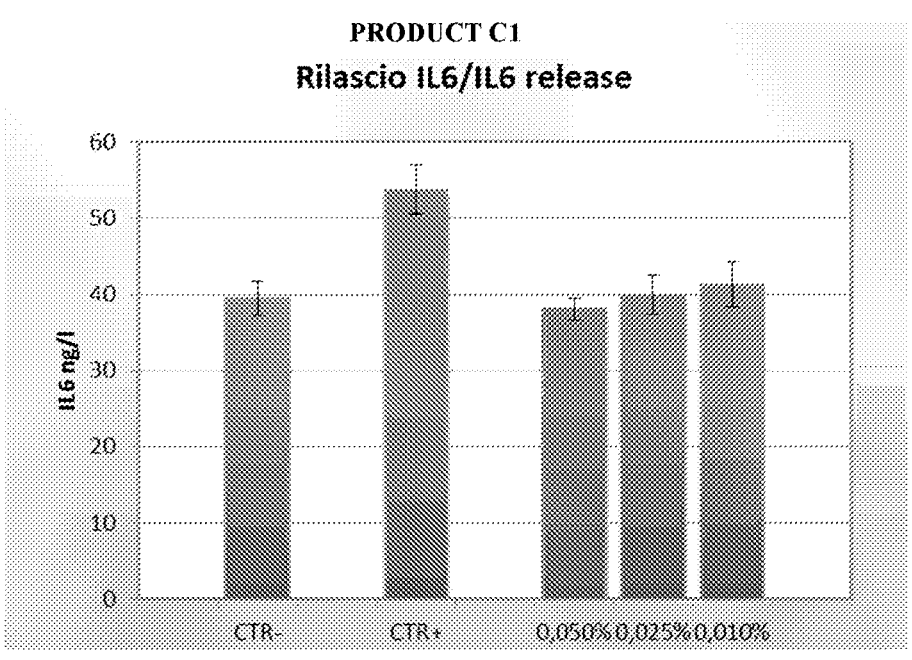
FIGS. 4a-4b-4c show the assays of IL6 in cell cultures for the compositions in question according to experimental part 3.
Figure 4B:
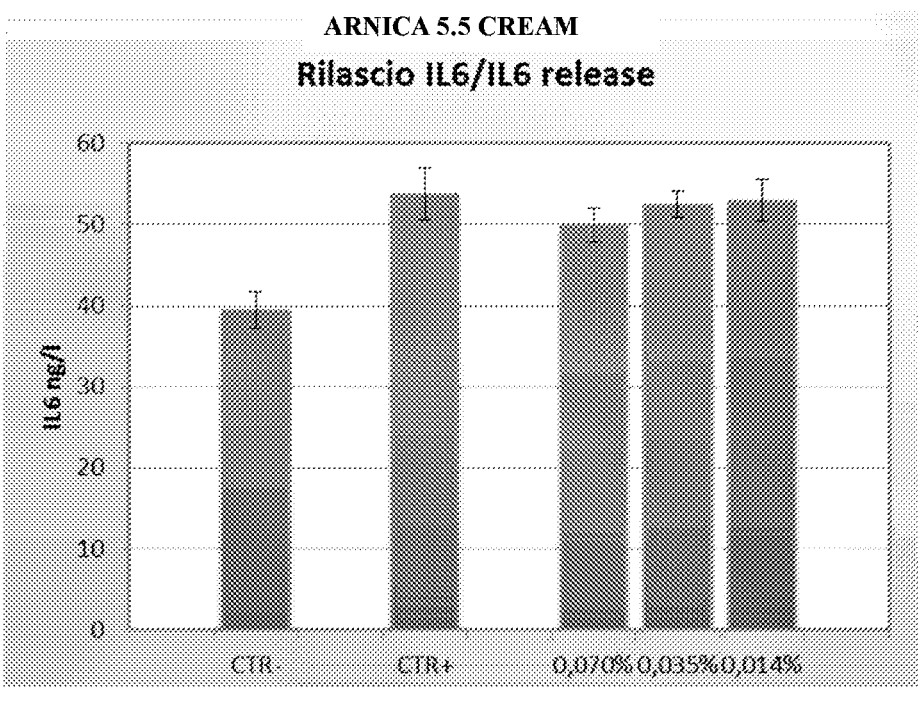
Figure 4C:
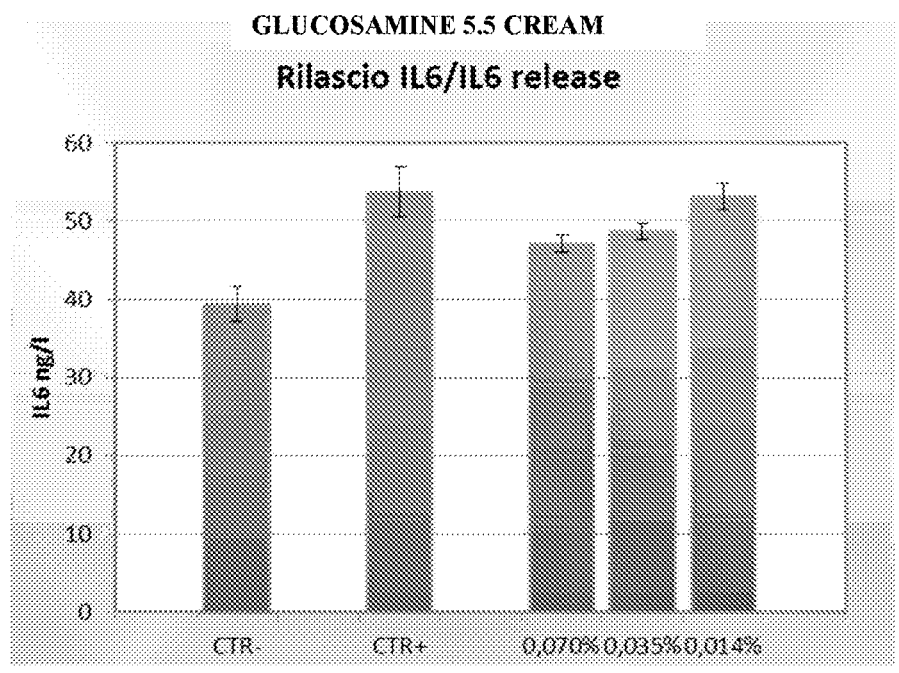

Treatment of cell cultures with the tested products (paragraph 2.) showed a reduction in levels of IL6 released by the cells following the experimental induction of inflammation (Tables 3-5 and FIGS. 4A, 4B and 4C). The tested samples more or less markedly modulate and inhibit the release of the pro-inflammatory cytokine monitored during inflammation. All the charts (FIGS. 4A, 4B and 4C) show a more or less evident dose-dependent trend, in which the highest concentration tested has the assay lower than IL6.

5.I. Assay of IL6 in the CTR−, CTR+ cell cultures and treated with the Cream Product C1 according to the present invention (Table 2). The results are expressed as mean content±std.dev. (expressed in ng/l) and as mean % variation as compared to the controls (Table 3 and FIG. 4A).

TABLE 3

| | IL6 ng/l | % Variation vs CTR− | % variation vs CTR+ |
|---|---|---|---|
| CTR− | 39.4 ± 2.3 | — | — |
| CTR+ | 53.8 ± 3.2 | +36.4% | — |
| CREAM Product C1 0.050% | 38.0 ± 1.5 | −3.5% | −29.3% |
| CREAM Product C1 0.025% | 39.9 ± 2.6 | +1.2% | −25.8% |
| CREAM Product C1 0.010% | 41.3 ± 3.0 | +4.9% | −23.1% |

5.II. Assay of IL6 in the CTR−, CTR+ cell cultures and treated with ARNICA Cream 5.5%. The results are expressed as mean content±std.dev. (expressed in ng/l) and as mean % variation as compared to the controls (Table 4 and FIG. 4B).

TABLE 4

| | IL6 ng/l | % Variation vs CTR− | % variation vs CTR+ |
|---|---|---|---|
| CTR− | 39.4 ± 2.3 | — | — |
| CTR+ | 53.8 ± 3.2 | +36.4% | — |
| ARNICA 5.5% CREAM 0.070% | 49.9 ± 2.1 | +26.7% | −7.1% |
| ARNICA 5.5% CREAM 0.035% | 52.5 ± 1.6 | +33.2% | −2.4% |
| ARNICA 5.5% CREAM 0.014% | 52.9 ± 2.5 | +34.4% | −1.5% |

5.III. Assay of IL6 in the CTR−, CTR+ cell cultures and treated with GLUCOSAMINE Cream 5.5%. The results are expressed as mean content±std.dev. (expressed in ng/l) and as mean % variation as compared to the controls (Table 5 and FIG. 4C).

TABLE 5

| | IL6 ng/l | % Variation vs CTR− | % variation vs CTR+ |
|---|---|---|---|
| CTR− | 39.4 ± 2.3 | — | — |
| CTR+ | 53.8 ± 3.2 | +36.4% | — |
| GLUCOSAMINE 5.5% CREAM 0.070% | 47.1 ± 1.1 | +19.7% | −12.3% |
| GLUCOSAMINE 5.5% CREAM 0.035% | 48.7 ± 1.0 | +23.5% | −9.5% |
| GLUCOSAMINE 5.5% CREAM 0.014% | 53.2 ± 1.7 | +35.0% | −1.1% |

Results for LTC4 Assay

Figure 5A:
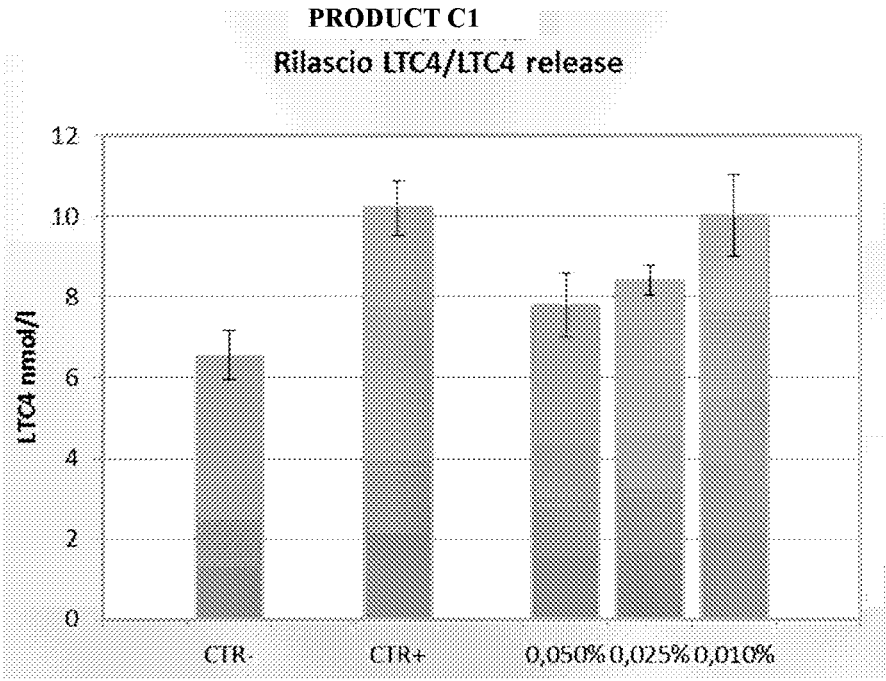
FIGS. 5a-5b-5c show the assays of LTC4 in cell cultures for the compositions in question according to experimental part 3.
Figure 5B:
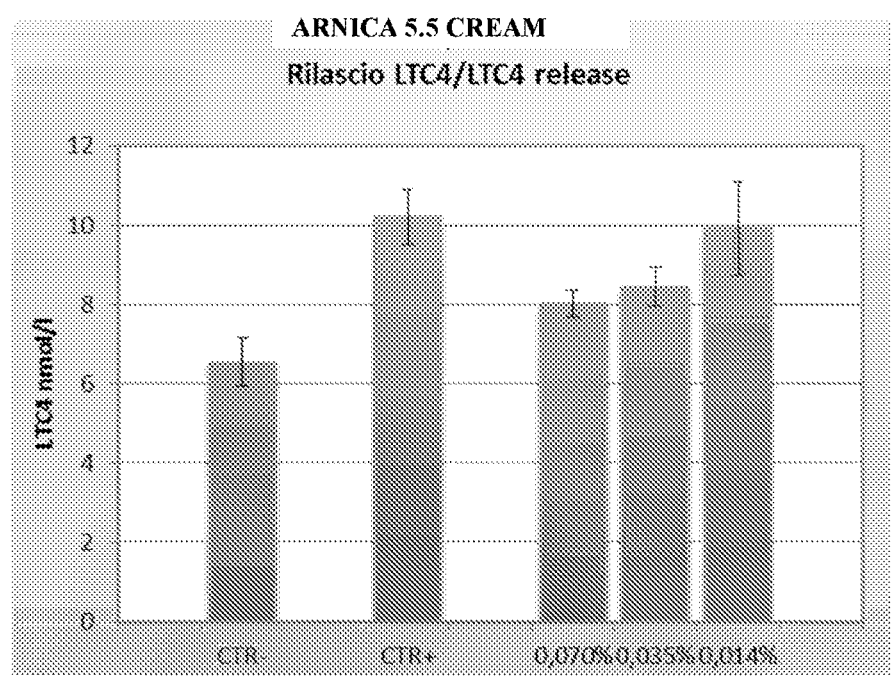
Figure 5C:
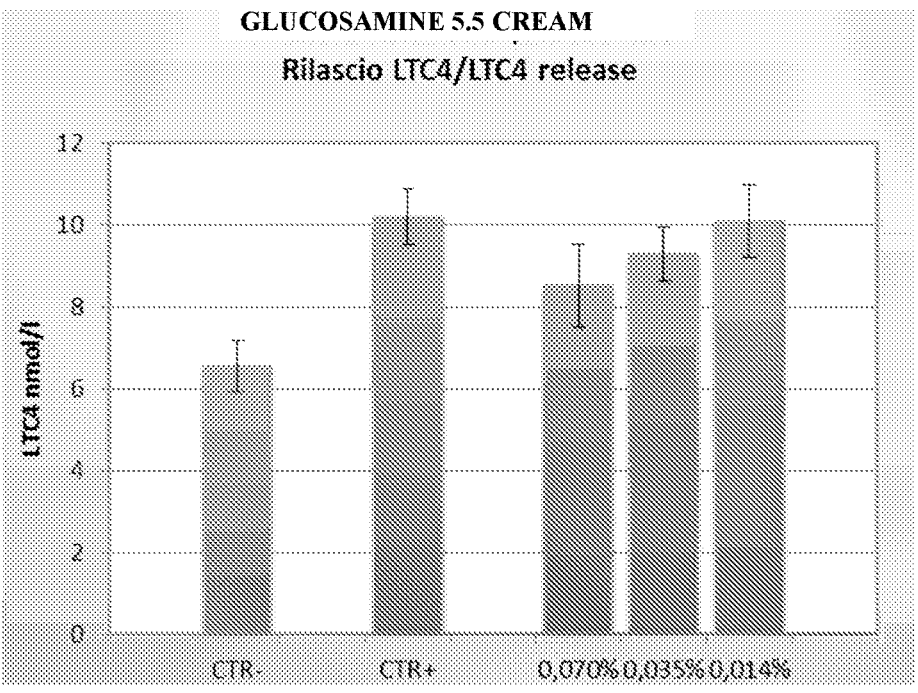

Treatment of cell cultures with the tested products (paragraph 2.) showed a reduction in levels of LTC4 released by the cells following the experimental induction of inflammation (Tables 6-8 and FIGS. 5A, 5B and 5C). The tested samples more or less markedly modulate and inhibit the release of the pro-inflammatory marker monitored during inflammation. All the charts (FIGS. 5A, 5B and 5C) show a more or less evident dose-dependent trend, in which the highest concentration tested has the assay lower than LTC4.

5.IV. Assay of LTC4 in the CTR−, CTR+ cell cultures and treated with the Cream Product C1 according to the present invention (Table 2). The results are expressed as mean content±std.dev. (expressed in ng/l) and as mean % variation as compared to the controls (Table 6 and FIG. 5A).

TABLE 6

| | LTC4 nmol/l | % Variation vs CTR− | % variation vs CTR+ |
|---|---|---|---|
| CTR− | 6.6 ± 0.6 | — | — |
| CTR+ | 10.2 ± 0.7 | +55.7% | — |
| CREAM Product C1 0.050% | 7.8 ± 0.8 | +19.1% | −23.5% |
| CREAM Product C1 0.025% | 8.4 ± 0.4 | +28.3% | −17.6% |
| CREAM Product C1 0.010% | 10.0 ± 1.0 | +52.8% | −1.8% |

5.V. Assay of LTC4 in the CTR−, CTR+ cell cultures and treated with ARNICA Cream 5.5%. The results are expressed as mean content±std.dev. (expressed in ng/l) and as mean % variation as compared to the controls (Table 7 and FIG. 5B).

TABLE 7

| | LTC4 nmol/l | % Variation vs CTR− | % variation vs CTR+ |
|---|---|---|---|
| CTR− | 6.6 ± 0.6 | — | — |
| CTR+ | 10.2 ± 0.7 | +55.7% | — |
| ARNICA 5.5% CREAM 0.070% | 8.0 ± 0.3 | +22.3% | −21.5% |
| ARNICA 5.5% CREAM 0.035% | 8.4 ± 0.5 | +28.9% | −17.2% |
| ARNICA 5.5% CREAM 0.014% | 9.9 ± 1.2 | +51.4% | −2.8% |

5.VI. Assay of LTC4 in the CTR−, CTR+ cell cultures and treated with GLUCOSAMINE Cream 5.5%. The results are expressed as mean content±std.dev. (expressed in ng/l) and as mean % variation as compared to the controls (Table 8 and FIG. 5C).

TABLE 8

| | LTC4 nmol/l | % Variation vs CTR− | % variation vs CTR+ |
|---|---|---|---|
| CTR− | 6.6 ± 0.6 | — | — |
| CTR+ | 10.2 ± 0.7 | +55.7% | — |
| GLUCOSAMINE 5.5% CREAM 0.070% | 8.5 ± 1.0 | +30.0% | −16.5% |
| GLUCOSAMINE 5.5% CREAM 0.035% | 9.3 ± 0.7 | +41.9% | −8.9% |
| GLUCOSAMINE 5.5% CREAM 0.014% | 10.1 ± 0.9 | +54.0% | −1.1% |

Results for PGE2 Assay

Figure 6A:
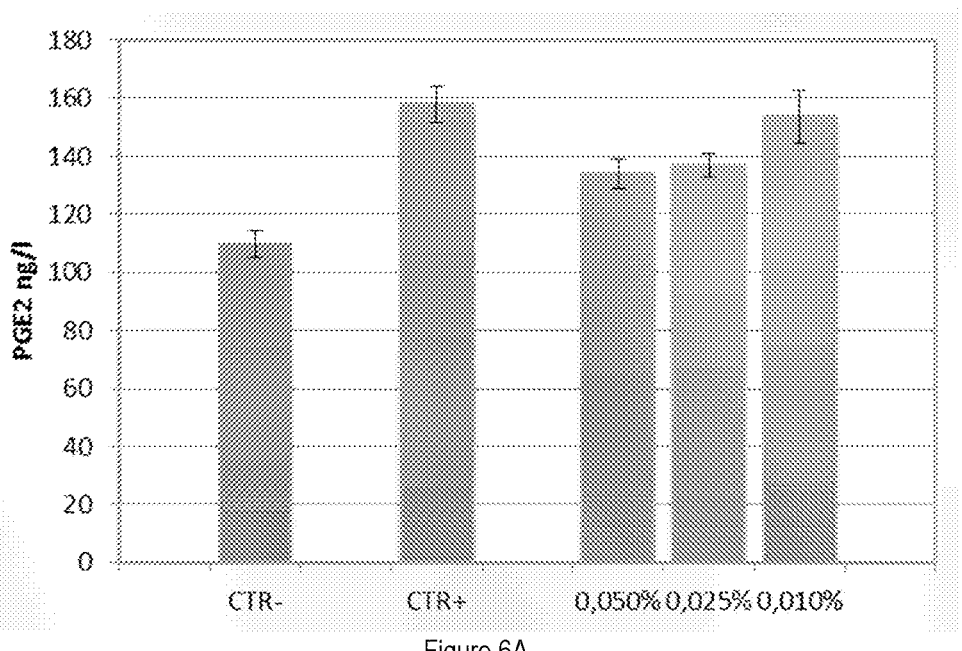
FIGS. 6a-6b-6c show the assays of PGE2 in cell cultures for the compositions in question according to experimental part 3.
Figure 6B:
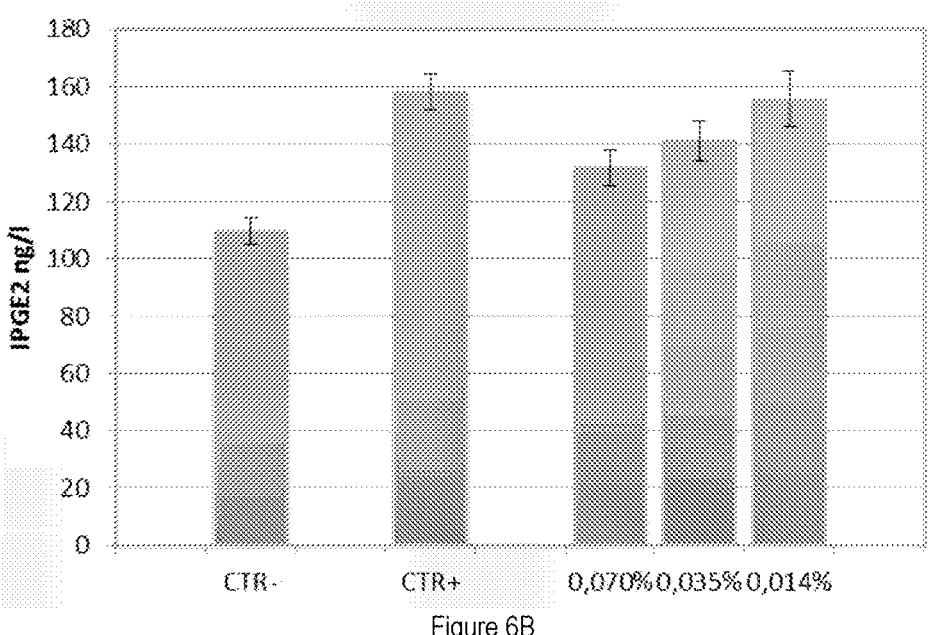
Figure 6C:
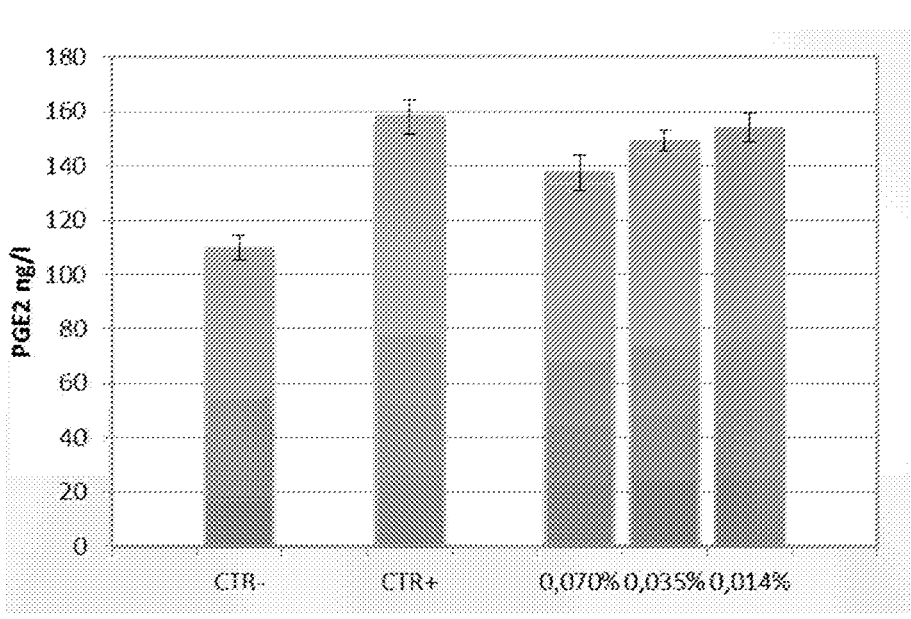

Treatment of cell cultures with the tested products (paragraph 2.) showed a reduction in levels of PGE2 released by the cells following the experimental induction of inflammation (Tables 9-11 and FIGS. 6A, 6B and 6C). The tested samples more or less markedly modulate and inhibit the release of the pro-inflammatory marker monitored during inflammation. All the charts (FIGS. 6A, 6B and 6C) show a more or less evident dose-dependent trend, in which the highest concentration tested has the assay lower than PGE2.

5.VII. Assay of PGE2 in the CTR−, CTR+ cell cultures and treated with the Cream Product C1 according to the present invention (Table 2). The results are expressed as mean content±std.dev. (expressed in ng/l) and as mean % variation as compared to the controls (Table 9 and FIG. 6A).

TABLE 9

| | PGE2 ng/l | % Variation vs CTR− | % variation vs CTR+ |
|---|---|---|---|
| CTR− | 109.8 ± 4.6 | — | — |
| CTR+ | 158.0 ± 6.3 | +43.8% | — |
| CREAM Product C1 0.050% | 134.0 ± 5.2 | +22.0% | −15.2% |
| CREAM Product C1 0.025% | 136.7 ± 4.2 | +24.5% | −13.4% |
| CREAM Product C1 0.010% | 153.6 ± 9.2 | +39.9% | −2.8% |

5.VIII. Assay of PGE2 in the CTR−, CTR+ cell cultures and treated with ARNICA Cream 5.5%. The results are expressed as mean content±std.dev. (expressed in ng/l) and as mean % variation as compared to the controls (Table 10 and FIG. 6B).

TABLE 10

| | PGE2 ng/l | % Variation vs CTR− | % variation vs CTR+ |
|---|---|---|---|
| CTR− | 109.8 ± 4.6 | — | — |
| CTR+ | 158.0 ± 6.3 | +43.8% | — |
| ARNICA 5.5% CREAM 0.070% | 131.7 ± 6.2 | +19.9% | −16.7% |
| ARNICA 5.5% CREAM 0.035% | 141.2 ± 7.0 | +28.6% | −10.6% |
| ARNICA 5.5% CREAM 0.014% | 155.7 ± 9.7 | +41.7% | −1.5% |

5.IX. Assay of PGE2 in the CTR−, CTR+ cell cultures and treated with GLUCOSAMINE Cream 5.5%. The results are expressed as mean content±std.dev. (expressed in ng/l) and as mean % variation as compared to the controls (Table 11 and FIG. 6C).

TABLE 11

| | PGE2 ng/l | % Variation vs CTR− | % variation vs CTR+ |
|---|---|---|---|
| CTR− | 109.8 ± 4.6 | — | — |
| CTR+ | 158.0 ± 6.3 | +43.8% | — |
| GLUCOSAMINE 5.5% CREAM 0.070% | 137.3 ± 6.6 | +25.0% | −13.1% |
| GLUCOSAMINE 5.5% CREAM 0.035% | 149.1 ± 3.9 | +35.8% | −5.6% |
| GLUCOSAMINE 5.5% CREAM 0.014% | 154.0 ± 5.4 | +40.2% | −2.5% |

6. CONCLUSIONS

Considering the results obtained and reported in this report and with reference to the experimental model applied, all the tested products modulated the inflammatory mechanisms induced in the cell culture, reducing the levels of the monitored pro-inflammatory markers and therefore showing anti-inflammatory activity. In particular, the Cream Product C1 and, also, the Cream Products C2-C6 according to the invention reduced the levels of IL-6, PGE2 and LTC4, thus proving to be capable of modulating the different amplification mechanisms.

The invention claimed is:

1. A method for protective treatment of a disorder or symptom deriving from and/or related with damaging gastric mucosa, selected from gastric ulcers, gastroesophageal reflux (GERD), and heartburn, the method comprising administering to a subject in need a composition in an effective amount to obtain gastric mucosal protection of the subject, the composition comprising:

(a) a mixture of at least one cetylated fatty acid, comprising, cetylated myristic acid and cetylated oleic acid, at a myristic:oleic mole ratio of about 2.1:1

(b) at least one antioxidant at a % by weight from 0.001% to 0.3% with respect to the total weight of the composition, and (c) a vegetable oil selected from olive oil, corn oil, mixtures thereof;

wherein the composition optionally further comprises at least one pharmaceutical or food grade additive and/or excipient.

2. The method according to claim 1, wherein said mixture of at least one cetylated fatty acid further comprises lauric acid, palmitic acid, palmitoleic acid, stearic acid, linoleic acid, eicosanoic acid, and mixtures thereof.

3. The method according to claim 1, wherein in said mixture of cetylated myristic acid and cetylated oleic acid the mole ratio between the cetylated myristic acid and cetylated oleic acid is from 4:1 to 1:1.

4. The method according to claim 1, wherein said at least one antioxidant is selected from tert-butyl-hydroquinone (TBHQ), a mixture comprising tocopherol, lecithin, ascorbyl palmitate and citric acid, and a mixture of tocopherols and a natural extract of rosemary.

5. The method according to claim 4, wherein the mixture comprising tocopherol, lecithin, ascorbyl palmitate and citric acid comprises a-tocopherol 10-15% by weight, lecithin >50% by weight, ascorbyl palmitate 8-10% by weight and citric acid <1% by weight.

6. The method according to claim 1, wherein said at least one antioxidant is present at a % by weight from 0.001% to 0.5% 0.1% with respect to the total weight of the composition.

7. The method according to claim 1, wherein said composition comprises: cetylated myristic acid and cetylated oleic acid and tert-butyl-hydroquinone (TBHQ).

8. The method according to claim 7, wherein the mole ratio between the cetylated myristic acid and cetylated oleic acid is from 4:1 to 1:1.

9. The method according to claim 7, wherein the mole ratio between the cetylated myristic acid and cetylated oleic acid is from 3:1 to 1.5:1.

10. The method according to claim 7, wherein the tert-butyl-hydroquinone (TBHQ) is present at a % by weight comprised from 0.001% to 0.5% with respect to the total weight of the composition.

11. The method according to claim 7, wherein the tert-butyl-hydroquinone (TBHQ) is present at a % by weight comprised from 0.005% to 0.1%, with respect to the total weight of the composition.

12. The method according to claim 1, wherein said composition is formulated for oral use.

13. The method according to claim 1, wherein the administering is performed by administering said composition as a coadjuvant of one or more additional compositions for protective treatment of the disorder or symptom deriving from and/or related with damaging the gastric mucosa.

14. The method according to claim 1, wherein said fatty acid of at least one cetylated fatty acid is selected from myristic acid, oleic acid or cetylated myristic acid and cetylated oleic acid and mixtures thereof.

15. The method according to claim 1, wherein in said mixture the mole ratio between the cetylated myristic acid and cetylated oleic acid is from 3:1 to 1.5:1.

16. The method according to claim 1, wherein said at least one antioxidant comprises tert-butyl-hydroquinone (TBHQ).

17. The method according to claim 1, wherein said at least one antioxidant is present at a % by weight from 0.005% to 0.1%, with respect to the total weight of the composition.

18. The method according to claim 1, wherein the vegetable oil further comprises, sunflower oil, or mixtures with high oleic or olein content.

* * * * *